(12) United States Patent
Tryggvason et al.

(10) Patent No.: US 12,391,915 B2
(45) Date of Patent: *Aug. 19, 2025

(54) MAINTENANCE OF DIFFERENTIATED CELLS WITH LAMININS

(71) Applicant: BioLamina AB, Sundyberg (SE)

(72) Inventors: Karl Tryggvason, Singapore (SG); Karl Kristian Tryggvason, Stockholm (SE); Anna Domogatskaya, Ronninge (SE)

(73) Assignee: BioLamina AB, Stockholm (SE)

( * ) Notice: Subject to any disclaimer, the term of this patent is extended or adjusted under 35 U.S.C. 154(b) by 34 days.

This patent is subject to a terminal disclaimer.

(21) Appl. No.: 17/511,079

(22) Filed: Oct. 26, 2021

(65) Prior Publication Data

US 2022/0041980 A1 Feb. 10, 2022

Related U.S. Application Data

(63) Continuation of application No. 15/351,124, filed on Nov. 14, 2016, now Pat. No. 11,155,781, which is a continuation of application No. 13/866,177, filed on Apr. 19, 2013, now Pat. No. 9,499,794.

(60) Provisional application No. 61/754,784, filed on Jan. 21, 2013, provisional application No. 61/716,005, filed on Oct. 19, 2012, provisional application No. 61/636,293, filed on Apr. 20, 2012, provisional application No. 61/636,211, filed on Apr. 20, 2012.

(51) Int. Cl.
*C12N 5/00* (2006.01)
*C12N 5/071* (2010.01)

(52) U.S. Cl.
CPC ......... *C12N 5/0068* (2013.01); *C12N 5/0676* (2013.01); *C12N 2501/998* (2013.01); *C12N 2533/52* (2013.01)

(58) Field of Classification Search
CPC ............ C12N 5/0068; C12N 2501/998; C12N 2533/52
See application file for complete search history.

(56) References Cited

U.S. PATENT DOCUMENTS

| | | | |
|---|---|---|---|
| 6,479,072 B1 * | 11/2002 | Morgan | A61L 15/42 435/284.1 |
| 2002/0081286 A1 * | 6/2002 | Marchionni | A61P 9/12 424/94.1 |
| 2003/0044899 A1 | 3/2003 | Tryggvason et al. | |

(Continued)

OTHER PUBLICATIONS

Amy Li, Normand Pouliot, Richard Redvers, Pritinder Kaur, Extensive tissue-regenerative capacity of neonatal human keratinocyte stem cells and their progeny, 2004, J. Clin. Invest., vol. 113, No. 3, pp. 390-400 (Year: 2004).*

(Continued)

*Primary Examiner* — David W Berke-Schlessel
*Assistant Examiner* — Trent R Clarke
(74) *Attorney, Agent, or Firm* — Lippes Mathias LLP

(57) ABSTRACT

The present disclosure describes methods of maintaining the phenotype of differentiated cells. Generally, the natural environment of the body is replicated for the differentiated cell. The differentiated cell is plated on a cell culture substrate comprising a laminin, such as laminin-521 or laminin-511. The substrate may also contain a cadherin. This maintains the phenotype of the differentiated cell.

25 Claims, 21 Drawing Sheets
(19 of 21 Drawing Sheet(s) Filed in Color)

(a)

(b)

(56) References Cited

U.S. PATENT DOCUMENTS

| | | | |
|---|---|---|---|
| 2008/0243239 A1 | 10/2008 | Dancu | |
| 2010/0233239 A1 | 9/2010 | Berkland et al. | |
| 2011/0091485 A1* | 4/2011 | Carter | C07K 16/28 |
| | | | 514/17.7 |
| 2012/0264209 A1 | 10/2012 | Odorico et al. | |
| 2013/0330825 A1* | 12/2013 | Couture | C12N 5/0657 |
| | | | 435/377 |
| 2014/0024677 A1* | 1/2014 | Schnellmann | A61K 31/138 |
| | | | 514/312 |
| 2015/0017718 A1* | 1/2015 | Nakatsuji | C07D 277/82 |
| | | | 435/363 |
| 2015/0125952 A1* | 5/2015 | Kim | A61L 27/3873 |
| | | | 435/396 |

OTHER PUBLICATIONS

Takashi Hoshiba, Katsumi Mochitate, Toshihiro Akaike, Hepatocytes maintain their function on basement membrane formed by epithelial cells, 2007, Biochemical and Biophysical Research Communications, vol. 359, pp. 151-156 (Year: 2007).*

Takashi Hoshiba, Mai Wakejima, Chong-Su Cho, Goshi Shiota, Toshihiro Akaike, Different regulation of hepatocyte behaviors between natural extracellular matrices and synthetic extracellular matrices by hepatocyte growth factor, 2008, J Biomed Mater Res, vol. 85A, pp. 228-235 (Year: 2008).*

Normand Pouliot, Nicholas A. Saunders and Pritinder Kaur, Laminin 10/11: an alternative adhesive ligand for epidermal keratinocytes with a functional role in promoting proliferation and migration, 2002, Experimental Dermatology, vol. 11, pp. 387-397 (Year: 2002).*

William NG and Shigaku Ikeda, Standardized, Defined Serum-free Culture of a Human Skin Equivalent on Fibroblast-populated Collagen Scaffold, 2011, Acta Derm Venereol, vol. 91, pp. 387-391 (Year: 2011).*

Banerjee Meenal et al., "Proliferation and plasticity of human beta cells on physiologically occurring laminin isoforms", Molecular and Cellular Endocrinology, vol. 355, No. 1, Jan. 31, 2012 (Jan. 31, 2012), pp. 78-86, XP002711864, ISSN: 0303-7207 p. 83, left-hand column, last paragraph-right-hand column, last paragraph; figure 5.

Zukowska-Grojec Zofia et al: "Neuropeptide Y. A novel angiogenic factor from the sympathetic nerves and endothelium", Circulation Research, Grune and Stratton, Baltimore, US, vol. 83, No. 2, Jul. 27, 1998 (Jul. 27, 1998), pp. 187-195, XP002958471, ISSN: 0009-7330 p. 188, left-hand column, last paragraph.

Michael Zeisberg et al: "De-differentiation of primary human hepatocytes depends on the composition of specialized liver basement membrane", Molecular and Cellular Biochemistry, Kluwer Academic Publishers, BO, vol. 283, No. 1-2, Feb. 1, 2006 (Feb. 1, 2006), pp. 181-189, XP019289028, ISSN: 1573-4919 p. 182, left-hand column, last paragraph-p. 183, left-hand column, paragraph 1.

Cotten M. et al., "Transferrin-Polycation-Mediated Introduction of DNA into Human Leukemic Ceels: Stimulation by Agents that Affect the Survival of Transfected DNA or Modulate Transferring Receptor Levels," PNAS, National Academy of Sciences, Jun. 1, 1990, pp. 4033-4037, vol. 87, US.

Miner, et al., "The Laminin alpha Chains: Expression, Developmental Transitions, and Chromosomal Locations of alpha 1-5, Identification of Heterotrimeric Laminins 8-11, and closing of a Novel alpha3 Isoform". The Journal of Cell Biology, vol. 137, No. 3, May 5, 1997. 685-701.

ThermoFishcer-William's E Medium, no phenol red. ThermoFisher Scientific. https://www.thermofisher.com/order/catalog/product/A1217601 Aug. 29, 2023.

Furuyama, et al., "Hepatocyte growth factor inhibits the formation of the basement membrane of alveolar epithelial cells in vitro". the American Physiological Society, Dec. 12, 2003.

Product Insert for Gibco Defined Keratinocyte SFM, TFS-Assets-LSG Manuals, copyright date of 2014.

Gibco Guide to Serum-Free Cell Culture, copyright date of 2003.

* cited by examiner

MAINTENANCE OF DIFFERENTIATED CELLS WITH LAMININS

This application is a continuation of U.S. patent application Ser. No. 15/351,124, filed on Nov. 14, 2016, now U.S. Pat. No. 11,155,781, which is a continuation of U.S. patent application Ser. No. 13/866,177, filed on Apr. 19, 2013, now U.S. Pat. No. 9,499,794, which claims priority to U.S. Provisional Patent Application Ser. No. 61/716,005, filed on Oct. 19, 2012; to U.S. Provisional Patent Application Ser. No. 61/754,784, filed on Jan. 21, 2013; to U.S. Provisional Patent Application Ser. No. 61/636,293, filed on Apr. 20, 2012; and to U.S. Provisional Patent Application Ser. No. 61/636,211, filed on Apr. 20, 2012. The disclosure of each of these applications is hereby fully incorporated by reference.

BACKGROUND

A stem cell is an undifferentiated cell from which specialized cells are subsequently derived. Examples of stem cells in the human body include pluripotent stem cells, embryonic stem cells, adult stem cells, fetal stem cells, and amniotic stem cells. Embryonic stem cells possess extensive self-renewal capacity and pluripotency with the potential to differentiate into cells of all three germ layers.

Totipotency refers to a cell that has the ability to differentiate into any cell in the body, including extraembryonic tissue. Pluripotency refers to a cell that has the potential to differentiate into cells of all three germ layers. Pluripotent cells however cannot form extraembryonic tissue, as a totipotent cell can. Multipotency refers to a cell that can differentiate into cells of limited lineage. For example, a hematopoietic stem cell can differentiate into several types of blood cells, but cannot differentiate into a brain cell.

The process by which a stem cell changes into a more specialized cell is referred to as differentiation. For example, some differentiated cells include endothelial cells, which are derived from endothelial stem cells.

The process by which a specialized cell reverts back to a higher degree of potency (i.e. to an earlier developmental stage) is referred to as dedifferentiation. In particular, cells in a cell culture can lose properties they originally had, such as protein expression or shape. It would be desirable to reduce the rate of dedifferentiation, or in other words to maintain the phenotype of differentiated cells in a cell culture.

BRIEF DESCRIPTION

Disclosed herein are methods for maintaining the phenotype of differentiated cells in a cell culture.

Described herein are methods for maintaining the phenotype of a differentiated cell, comprising: plating the differentiated cell on a cell culture substrate comprising a laminin, wherein the laminin is an intact protein or a protein fragment.

The differentiated cell can be an endothelial cell, a cardiomyocyte, a dopamine producing cell, a hepatocyte, or a pancreatic beta cell.

The laminin may be laminin-521 or laminin-511, or an effective recombinant laminin.

The cell culture substrate may further comprise a cadherin. Sometimes, the cadherin is e-cadherin. The weight ratio of the laminin to the cadherin can be from about 5:1 to about 15:1, or from about 5:1 to about 10:1. In particular embodiments, the laminin is laminin-521 and the cadherin is e-cadherin. In other embodiments, the cell culture substrate consists of the laminin and the cadherin. Generally, the cell culture substrate does not contain any differentiation inhibitors, feeder cells, differentiation inductors, or apoptosis inhibitors.

The method may further include applying a cell culture medium to the first stem cell. In specific embodiments, the cell culture medium has an albumin concentration of at least 0.3 mM.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
FIG. 1 is a rotary shadowing electron microscopy picture of a recombinant laminin molecule.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

Unless otherwise stated, the techniques utilized in this application may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

The methods of the present disclosure are generally related to maintaining the phenotype of differentiated cells. The term "phenotype" here refers to the cell's observable characteristics and properties. These include such things as the cell's morphology, biochemical or physiological properties, etc. It is desirable to maintain the cell's phenotype.

It is contemplated that any kind of differentiated cell can be maintained with the methods of the present disclosure. Examples of differentiated cells include endothelial cells, cardiomyocytes, dopamine producing cells, hepatocytes, and pancreatic beta cells, though of course other differentiated cells are contemplated. Generally speaking, the present disclosure creates a natural environment for the differentiated cell using laminins that are close to the differentiated cell in the body.

The methods of the present disclosure also relate to improving the transfection efficiency of primary cells and/or survival rate of transfected cells. The primary cells are plated on a substrate containing a laminin, wherein the laminin is an intact protein or a protein fragment. The primary cells are then transfected with a vector, and the transfected cells are cultured on the substrate.

The term "primary cells" refers in the art to cells which are taken directly from a subject. Such cells generally are not immortal, and have a limited lifespan, or in other words they stop dividing though they retain viability. Exemplary primary cells include hepatocytes, adipocytes, podocytes, chondrocytes, melanocytes, keratinocytes, and laminins. Primary cells are also differentiated cells.

Differentiated cells typically require two things to survive and reproduce: (1) a substrate or coating that provides a structural support for the cell; and (2) a cell culture medium to provide nutrition to the cell. The substrate or coating (1) is typically formed as a layer in a container, for example a petri dish or in the well of a multi-well plate. It is particularly contemplated that the cell culture substrate on which the differentiated cell is plated comprises a laminin and a cadherin.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

Figure 2:
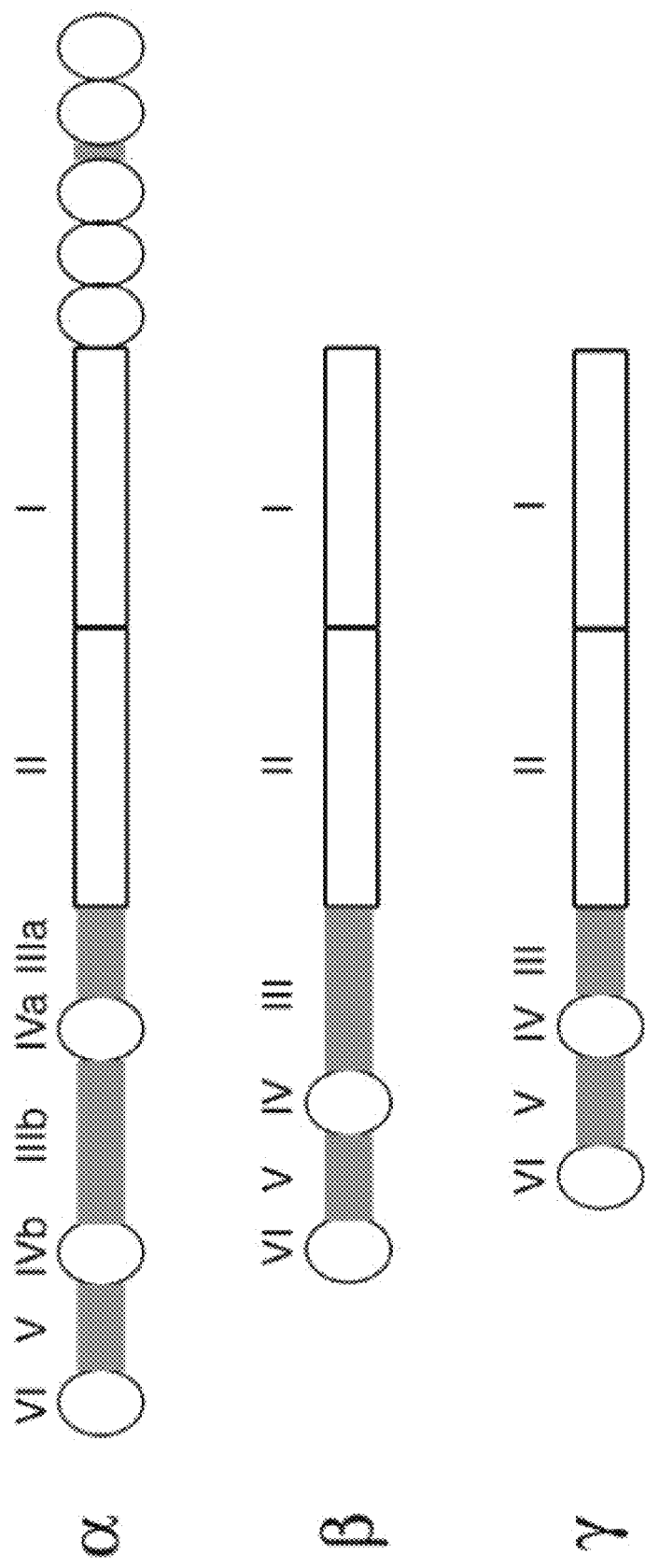
FIG. 2 shows the structural motifs of laminin α, β, and γ chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A laminin protein molecule comprises one α-chain subunit, one β-chain subunit, and one γ-chain subunit, all joined together in a trimer through a coiled-coil domain. FIG. 1 depicts the resulting structure of the laminin molecule. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 2 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the $\beta1$ and $\gamma1$ chains, and vary by their $\alpha$-chain composition ($\alpha1$ to $\alpha5$ chain). The second group of five identified laminin molecules, including laminin-521, all share the $\beta2$ and $\gamma1$ chain, and again vary by their $\alpha$-chain composition. The third group of identified laminin molecules has one identified member, laminin-332, with a chain composition of $\alpha3\beta3\gamma2$. The fourth group of identified laminin molecules has one identified member, laminin-213, with the newly identified $\gamma3$ chain ($\alpha2\beta1\gamma3$).

Generally, the cell culture substrate may contain any effective laminin, wherein the effectiveness is determined by whether differentiated cells can survive upon the substrate. It is specifically contemplated that the substrate contains only one particular laminin, though other ingredients are also present in the substrate. In specific embodiments, the laminin is laminin-521 (LN-521) or laminin-511 (LN-511).

The term "laminin-521" refers to the protein formed by joining $\alpha5$, $\beta2$ and $\gamma1$ chains together. The term "laminin-511" refers to the protein formed by joining $\alpha5$, $\beta1$ and $\gamma1$ chains together. These terms should be construed as encompassing both the recombinant laminin and heterotrimeric laminin from naturally occurring sources. The term "recombinant" indicates that the protein is artificially produced in cells that do not normally express such proteins.

The laminin can be an intact protein or a protein fragment. The term "intact" refers to the protein being composed of all of the domains of the $\alpha$-chain, $\beta$-chain, and $\gamma$-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

The average contact area and spreading homogeneity is much larger for cells cultured on laminin-511 compared to other available substrata.

In particular, it is noted that the pancreatic insulin-producing islets are naturally in the shape of a three-dimensional sphere. However, a petri dish typically only provides two dimensions for growth, which means that it is difficult to expand the islets using a mechanical split. Beta cells within the islets form syncytium-like structures, and beta cells will respond simultaneously to external signals. When cultured as single cells, though, beta cells lose this natural function of simultaneous response.

The cell culture substrate also comprises a cadherin. Cadherins are a class of type-1 transmembrane proteins that play important roles in cell adhesion, ensuring that cells within tissues are bound together. They are dependent on calcium ($Ca^{2+}$) ions to function. Cadherins are also known as desmogleins and desmocollins. Structurally, cadherins contain extracellular $Ca^{2+}$-binding domains. In particular embodiments, the cadherin used in the cell culture substrate is epithelial cadherin or e-cadherin.

The weight ratio of the laminin to the cadherin may be from about 5:1 to about 15:1, or from about 5:1 to about 10:1. In particular embodiments, the cell culture substrate consists of the laminin and the cadherin. In other specific embodiments, the laminin is laminin-521 and the cadherin is e-cadherin.

The cell culture substrate is used in combination with a cell culture medium. The cell culture medium of the present disclosure is particularly suitable for being used with a substrate that contains laminin-521 and/or laminin-511. These laminins activate $\alpha6\beta1$ integrins, which in turn leads to activation of the PI3K/Akt pathway. This increases the pluripotency, self-renewal, and/or proliferation of the differentiated cells. It is contemplated that the substrate may consist of laminin-521 or laminin-511, either intact, as separate chains, or as fragments thereof. Recombinant laminin-521 and recombinant laminin-511 are commercially available; see for example U.S. Pat. No. 8,415,156, which provides amino acid sequences and DNA sequences for LN-521, and the entirety of which is incorporated by reference herein. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via $\alpha6\beta1$ integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Very generally, the cell culture medium of the present disclosure requires lower amounts of basic fibroblast growth factor (bFGF) than typically used. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E-01" should be interpreted as $4.1\times10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E-01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E-01 | 1.5E+00 | 2.1E+04 | 6.2E+04 |
| Magnesium chloride (Anhydrous) | 95.21 | 1.2E-01 | 3.6E-01 | 1.1E+04 | 3.4E+04 |
| Magnesium Sulfate (MgSO$_4$) | 120.37 | 1.6E-01 | 4.8E-01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate (NaHCO$_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E-01 | 5.9E-01 | 2.8E+04 | 8.3E+04 |
| Sodium phosphate, monobasic monohydrate (NaH$_2$PO$_4$E—H$_2$O) | 137.99 | 1.8E-01 | 5.3E-01 | 2.4E+04 | 7.3E+04 |
| TRACE MINERALS | | | | | |
| Ferric Nitrate (Fe(NO$_3$)$_3$—9H$_2$O) | 404 | 4.9E-05 | 1.9E-04 | 2.0E+01 | 7.5E+01 |
| Ferrous sulfate heptahydrate (FeSO$_4$—7H$_2$O) | 278.01 | 5.9E-04 | 1.8E-03 | 1.6E+02 | 4.9E+02 |
| Copper(II) sulfate pentahydrate (CuSO$_4$—5H$_2$O) | 249.69 | 2.0E-06 | 8.0E-06 | 5.1E-01 | 2.0E+00 |
| Zinc sulfate heptahydrate (ZnSO$_4$—7H$_2$O) | 287.56 | 5.9E-04 | 1.8E-03 | 1.7E+02 | 5.1E+02 |
| Ammonium Metavanadate NH$_4$VO$_3$ | 116.98 | 5.5E-06 | 1.6E-05 | 6.4E-01 | 1.9E+00 |
| Manganese Sulfate monohydrate (MnSO$_4$—H$_2$O) | 169.02 | 9.9E-07 | 3.0E-06 | 1.7E-01 | 5.0E-01 |
| NiSO$_4$—6H$_2$O | 262.85 | 4.9E-07 | 1.5E-06 | 1.3E-01 | 3.8E-01 |
| Selenium | 78.96 | 8.9E-05 | 2.7E-04 | 7.0E+00 | 2.1E+01 |
| Sodium Meta Silicate Na$_2$SiO$_3$—9H$_2$O | 284.2 | 4.8E-04 | 1.4E-03 | 1.4E+02 | 4.1E+02 |
| SnCl$_2$ | 189.62 | 6.2E-07 | 1.9E-06 | 1.2E-01 | 3.5E-01 |
| Molybdic Acid, Ammonium salt | 1235.86 | 9.9E-07 | 3.0E-06 | 1.2E+00 | 3.7E+00 |
| CdCl$_2$ | 183.32 | 6.1E-06 | 1.8E-05 | 1.1E+00 | 3.4E+00 |
| CrCl$_3$ | 158.36 | 9.9E-07 | 3.0E-06 | 1.6E-01 | 4.7E-01 |
| AgNO$_3$ | 169.87 | 4.9E-07 | 1.5E-06 | 8.3E-02 | 2.5E-01 |
| AlCl$_3$—6H$_2$O | 241.43 | 2.4E-06 | 7.3E-06 | 5.9E-01 | 1.8E+00 |
| Barium Acetate (Ba(C$_2$H$_3$O$_2$)$_2$) | 255.42 | 4.9E-06 | 1.5E-05 | 1.3E+00 | 3.8E+00 |
| CoCl$_2$—6H$_2$O | 237.93 | 4.9E-06 | 1.5E-05 | 1.2E+00 | 3.5E+00 |
| GeO$_2$ | 104.64 | 2.5E-06 | 7.5E-06 | 2.6E-01 | 7.8E-01 |
| KBr | 119 | 4.9E-07 | 1.5E-06 | 5.9E-02 | 1.8E-01 |
| KI | 166 | 5.0E-07 | 1.5E-06 | 8.3E-02 | 2.5E-01 |
| NaF | 41.99 | 4.9E-05 | 1.5E-04 | 2.1E+00 | 6.2E+00 |
| RbCl | 120.92 | 4.9E-06 | 1.5E-05 | 5.9E-01 | 1.8E+00 |
| ZrOCl$_2$—8H$_2$O | 178.13 | 4.9E-06 | 1.5E-05 | 8.7E-01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E-01 | 5.9E-01 | 2.2E+04 | 6.5E+04 |
| LIPIDS | | | | | |
| Linoleic Acid | 280.45 | 9.4E-05 | 2.8E-04 | 2.6E+01 | 7.9E+01 |
| Lipoic Acid | 206.33 | 2.0E-04 | 7.8E-04 | 4.1E+01 | 1.6E+02 |
| Arachidonic Acid | 304.47 | 6.5E-06 | 1.9E-05 | 2.0E+00 | 5.9E+00 |
| Cholesterol | 386.65 | 5.6E-04 | 1.7E-03 | 2.2E+02 | 6.5E+02 |
| DL-alpha tocopherol-acetate | 472.74 | 1.5E-04 | 4.4E-04 | 6.9E+01 | 2.1E+02 |
| Linolenic Acid | 278.43 | 3.5E-05 | 1.0E-04 | 9.7E+00 | 2.9E+01 |
| Myristic Acid | 228.37 | 4.3E-05 | 1.3E-04 | 9.8E+00 | 2.9E+01 |
| Oleic Acid | 282.46 | 3.5E-05 | 1.0E-04 | 9.8E+00 | 2.9E+01 |
| Palmitic Acid | 256.42 | 3.8E-05 | 1.1E-04 | 9.8E+00 | 2.9E+01 |
| Palmitoleic acid | 254.408 | 3.9E-05 | 1.2E-04 | 9.8E+00 | 2.9E+01 |
| Stearic Acid | 284.48 | 3.4E-05 | 1.0E-04 | 9.8E+00 | 2.9E+01 |
| AMINO ACIDS | | | | | |
| L-Alanine | 89.09 | 2.5E-02 | 2.1E-01 | 2.2E+03 | 1.8E+04 |
| L-Arginine hydrochloride | 147.2 | 2.7E-01 | 1.5E+00 | 4.0E+04 | 2.2E+05 |
| L-Asparagine-H$_2$O | 150.13 | 5.0E-02 | 2.1E-01 | 7.5E+03 | 3.1E+04 |
| L-Aspartic acid | 133.1 | 2.5E-02 | 2.1E-01 | 3.3E+03 | 2.7E+04 |
| L-Cysteine-HCl—H$_2$O | 175.63 | 3.9E-02 | 1.2E-01 | 6.9E+03 | 2.1E+04 |
| L-Cystine dihydrochloride | 313.22 | 3.9E-02 | 1.2E-01 | 1.2E+04 | 3.7E+04 |
| L-Glutamic acid | 147.13 | 2.5E-02 | 2.1E-01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E-01 | 4.4E-01 | 1.1E+04 | 3.3E+04 |
| L-Histidine monohydrochloride monohydrate | 209.63 | 5.9E-02 | 1.8E-01 | 1.2E+04 | 3.7E+04 |
| L-Isoleucine | 131.17 | 1.6E-01 | 4.9E-01 | 2.1E+04 | 6.4E+04 |
| L-Leucine | 131.17 | 1.8E-01 | 5.3E-01 | 2.3E+04 | 7.0E+04 |
| L-Lysine hydrochloride | 182.65 | 2.0E-01 | 5.9E-01 | 3.6E+04 | 1.1E+05 |
| L-Methionine | 149.21 | 4.5E-02 | 1.4E-01 | 6.8E+03 | 2.0E+04 |
| L-Phenylalanine | 165.19 | 8.5E-02 | 2.5E-01 | 1.4E+04 | 4.2E+04 |
| L-Proline | 115.13 | 1.1E-01 | 3.2E-01 | 1.2E+04 | 3.7E+04 |
| L-Serine | 105.09 | 1.5E-01 | 4.4E-01 | 1.5E+04 | 4.6E+04 |
| L-Threonine | 119.12 | 1.8E-01 | 5.3E-01 | 2.1E+04 | 6.3E+04 |
| L-Tryptophan | 204.23 | 1.7E-02 | 5.2E-02 | 3.5E+03 | 1.1E+04 |
| L-Tyrosine disodium salt hydrate | 225.15 | 8.4E-02 | 3.7E-01 | 1.9E+04 | 8.4E+04 |
| L-Valine | 117.15 | 1.8E-01 | 5.3E-01 | 2.1E+04 | 6.2E+04 |
| VITAMINS | | | | | |
| Ascorbic acid | 176.12 | 1.3E-01 | 3.8E-01 | 2.2E+04 | 6.7E+04 |
| Biotin | 244.31 | 5.6E-06 | 1.7E-05 | 1.4E+00 | 4.1E+00 |
| B$_{12}$ | 1355.37 | 2.0E-04 | 5.9E-04 | 2.7E+02 | 8.0E+02 |
| Choline chloride | 139.62 | 2.5E-02 | 7.5E-02 | 3.5E+03 | 1.1E+04 |
| D-Calcium pantothenate | 238.27 | 1.8E-03 | 1.4E-02 | 4.4E+02 | 3.4E+03 |
| Folic acid | 441.4 | 2.4E-03 | 7.1E-03 | 1.0E+03 | 3.1E+03 |
| idnositol | 180.16 | 2.7E-02 | 1.1E-01 | 4.9E+03 | 1.9E+04 |
| Niacinamide | 122.12 | 6.5E-03 | 2.0E-02 | 7.9E+02 | 2.4E+03 |
| Pyridoxine hydrochloride | 205.64 | 3.8E-03 | 1.1E-02 | 7.8E+02 | 2.4E+03 |
| Riboflavin | 376.36 | 2.3E-04 | 6.8E-04 | 8.6E+01 | 2.6E+02 |
| Thiamine hydrochloride | 337.27 | 3.3E-03 | 3.6E-02 | 1.1E+03 | 1.2E+04 |
| GROWTH FACTORS/ PROTEINS | | | | | |
| GABA | 103.12 | 0 | 1.5E+00 | 0 | 1.5E+05 |
| Pipecolic Acid | 129 | 0 | 1.5E-03 | 0 | 1.9E+02 |
| bFGF | 18000 | 0 | 2.17E-07 | 0 | 3.9E+00 |
| TGF beta 1 | 25000 | 0 | 3.5E-08 | 0 | 8.8E-01 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute. However, in more specific embodiments, it is contemplated that the cell culture medium may not (1) insulin or insulin substitute, or (2) transferrin or transferrin substitute, or any combination of these two components.

It should be noted that other cell culture mediums may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (μg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | μg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
|---|---|
| Glycine | 7.50E+03 |
| L-Alanine | 8.90E+03 |
| L-Asparagine | 1.32E+04 |
| L-Aspartic acid | 1.33E+04 |

TABLE 3-continued

| MEM Amino Acids | Concentration (ng/mL) |
|---|---|
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
|---|---|
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

In particular, the cell culture medium may have an albumin concentration of at least 0.3 millimolar (mM). It has been found that a 2× increase in albumin concentration significantly improved clonal survival of human embryonic stem cells on a laminin-521/E-Cadherin matrix. Table 5 below provides a formulation for a cell culture medium containing additional albumin.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E-01 |
| HEPES | 238.3 | 2.81E+06 | 1.18E+01 |
| Lithium Chloride (LiCl) | 42.39 | 4.15E+04 | 9.80E-01 |
| Magnesium chloride (Anhydrous) | 95.21 | 2.26E+04 | 2.37E-01 |
| Magnesium Sulfate (MgSO$_4$) | 120.37 | 3.84E+04 | 3.19E-01 |
| Potassium chloride (KCl) | 74.55 | 2.43E+05 | 3.26E+00 |
| Sodium bicarbonate (NaHCO$_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E-01 |
| Sodium phosphate, monobasic monohydrate (NaH$_2$PO$_4$—H$_2$O) | 137.99 | 4.90E+04 | 3.55E-01 |
| TRACE MINERALS | | | |
| Ferric Nitrate (Fe(NO$_3$)$_3$—9H$_2$O) | 404 | 3.92E+01 | 9.71E-05 |
| Ferrous sulfate heptahydrate (FeSO$_4$—7H$_2$O) | 278.01 | 3.28E+02 | 1.18E-03 |
| Copper(II) sulfate pentahydrate (CuSO$_4$—5H$_2$O) | 249.69 | 1.02E+00 | 4.08E-06 |
| Zinc sulfate heptahydrate (ZnSO$_4$—7H$_2$O) | 287.56 | 3.39E+01 | 1.18E-03 |
| Ammonium Metavanadate NH$_4$VO$_3$ | 116.98 | 1.28E+00 | 1.09E-05 |
| Manganese Sulfate monohydrate (MnSO$_4$—H$_2$O) | 169.02 | 3.33E-01 | 1.97E-06 |
| NiSO$_4$—6H$_2$O | 262.85 | 2.55E-01 | 9.70E-07 |
| Selenium | 78.96 | 1.40E+01 | 1.77E-04 |
| Sodium Meta Silicate Na$_2$SiO$_3$ 9H$_2$O | 284.2 | 2.75E+02 | 9.66E-04 |
| SnCl$_2$ | 189.62 | 2.35E-01 | 1.24E-06 |
| Molybdic Acid, Ammonium salt | 1235.86 | 2.43E+00 | 1.97E-06 |
| CdCl$_2$ | 183.32 | 2.24E+00 | 1.22E-05 |
| CrCl$_3$ | 158.36 | 3.14E-01 | 1.98E-06 |
| AgNO$_3$ | 169.87 | 1.67E-01 | 9.81E-07 |
| AlCl$_3$ 6H$_2$O | 241.43 | 1.18E+00 | 4.87E-06 |
| Barium Acetate (Ba(C$_2$H$_3$O$_2$)$_2$) | 255.42 | 2.50E+00 | 9.79E-06 |
| CoCl$_2$ 6H$_2$O | 237.93 | 2.33E+00 | 9.81E-06 |
| GeO$_2$ | 104.64 | 5.20E-01 | 4.97E-06 |
| KBr | 119 | 1.18E-01 | 9.89E-07 |
| KI | 166 | 1.66E-01 | 1.00E-06 |
| NaF | 41.99 | 4.13E+00 | 9.83E-05 |
| RbCl | 120.92 | 1.19E+00 | 9.81E-06 |
| ZrOCl$_2$ 8H$_2$O | 178.13 | 1.75E+00 | 9.80E-06 |
| ENERGY SUBSTRATES | | | |
| D-Glucose | 180.16 | 2.47E+06 | 1.37E+01 |
| Sodium Pyruvate | 110.04 | 4.31E+04 | 3.92E-01 |
| LIPIDS | | | |
| Linoleic Acid | 280.45 | 5.27E+01 | 1.88E-04 |
| Lipoic Acid | 206.33 | 8.25E+01 | 4.00E-04 |
| Arachidonic Acid | 304.47 | 3.93E+00 | 1.29E-05 |
| Cholesterol | 386.65 | 4.33E+02 | 1.12E-03 |
| DL-alpha tocopherol-acetate | 472.74 | 1.37E+02 | 2.90E-04 |
| Linolenic Acid | 278.43 | 1.95E+01 | 6.99E-05 |
| Myristic Acid | 228.37 | 1.96E+01 | 8.59E-05 |
| Oleic Acid | 282.46 | 1.96E+01 | 6.94E-05 |
| Palmitic Acid | 256.42 | 1.96E+01 | 7.65E-05 |
| Palmitoleic acid | 254.408 | 1.96E+01 | 7.71E-05 |
| Stearic Acid | 284.48 | 1.96E+01 | 6.89E-05 |
| AMINO ACIDS | | | |
| L-Alanine | 89.09 | 1.22E+04 | 1.37E-01 |
| L-Arginine hydrochloride | 147.2 | 8.07E+04 | 5.48E-01 |
| L-Asparagine-H$_2$O | 150.13 | 2.06E+04 | 1.37E-01 |
| L-Aspartic acid | 133.1 | 1.82E+04 | 1.37E-01 |
| L-Cysteine-HCl—H$_2$O | 175.63 | 1.38E+04 | 7.83E-02 |
| L-Cystine dihydrochloride | 313.22 | 2.45E+04 | 7.83E-02 |
| L-Glutamic acid | 147.13 | 2.02E+04 | 1.37E-01 |
| L-Glutamine | 146.15 | 4.30E+05 | 2.94E+00 |
| Glycine | 75.07 | 2.21E+04 | 2.94E-01 |
| L-Histidine monohydrochloride monohydrate | 209.63 | 2.47E+04 | 1.18E-01 |
| L-Isoleucine | 131.17 | 4.28E+04 | 3.26E-01 |
| L-Leucine | 131.17 | 4.64E+04 | 3.54E-01 |
| L-Lysine hydrochloride | 182.65 | 7.14E+04 | 3.91E-01 |
| L-Methionine | 149.21 | 1.35E+04 | 9.06E-02 |
| L-Phenylalanine | 165.19 | 2.79E+04 | 1.69E-01 |
| L-Proline | 115.13 | 2.49E+04 | 2.16E-01 |
| L-Serine | 105.09 | 3.09E+04 | 2.94E-01 |
| L-Threonine | 119.12 | 4.19E+04 | 3.52E-01 |
| L-Tryptophan | 204.23 | 7.07E+03 | 3.46E-02 |
| L-Tyrosine disodium salt hydrate | 225.15 | 3.78E+04 | 1.68E-01 |
| L-Valine | 117.15 | 4.16E+04 | 3.55E-01 |
| VITAMINS | | | |
| Ascorbic acid | 176.12 | 4.46E+04 | 2.53E-01 |
| Biotin | 244.31 | 2.74E+00 | 1.12E-05 |
| B12 | 1355.37 | 5.34E+02 | 3.94E-04 |
| Choline chloride | 139.62 | 7.02E+03 | 5.03E-02 |
| D-Calcium pantothenate | 238.27 | 8.79E+02 | 3.69E-03 |
| Folic acid | 441.4 | 2.08E+03 | 4.71E-03 |
| i-Inositol | 180.16 | 9.89E+03 | 5.49E-02 |
| Niacinamide | 122.12 | 1.59E+03 | 1.30E-02 |
| Pyridoxine hydrochloride | 205.64 | 1.57E+03 | 7.62E-03 |
| Riboflavin | 376.36 | 1.72E+02 | 4.56E-04 |
| Thiamine hydrochloride | 337.27 | 8.16E+03 | 2.42E-02 |
| GROWTH FACTORS/PROTEINS | | | |
| GABA | 103.12 | 1.01E+05 | 9.79E-01 |
| Pipecolic Acid | 129 | 1.27E+02 | 9.84E-04 |
| bFGF | 18000 | 1.04E+02 | 5.77E-06 |
| TGF beta 1 | 25000 | 5.88E-01 | 2.35E-08 |
| Human Insulin | 5808 | 2.28E+04 | 3.92E-03 |
| Human Holo-Transferrin | 78500 | 1.08E+04 | 1.37E-04 |
| Human Serum Albumin | 67000 | 1.31E+07 | 1.95E-01 |
| Glutathione (reduced) | 307.32 | 1.96E+03 | 6.38E-03 |
| OTHER COMPONENTS | | | |
| Hypoxanthine Na | 136.11 | 1.61E+03 | 1.18E-02 |
| Phenol red | 354.38 | 5.99E+03 | 1.69E-02 |
| Putrescine-2HCl | 161.07 | 6.36E+01 | 3.95E-04 |
| Thymidine | 242.229 | 2.86E+02 | 1.18E-03 |
| 2-mercaptoethanol | 78.13 | 7.66E+03 | 9.80E-02 |
| Pluronic F-68 | 8400 | 1.96E+05 | 2.33E-02 |
| Tween 80 | 1310 | 4.31E+02 | 3.29E-04 |

The systems containing a LN-521/e-cadherin substrate and mTeSR1 medium with additional albumin work extremely well for maintaining the differentiated cells in their phenotype in a completely chemically defined environment and xeno-free conditions without feeders or any inhibitors of apoptosis.

It is contemplated that the cell culture medium will be completely defined and xeno-free. The medium should also be devoid of any differentiation inhibitors, feeder cells, or differentiation inductors, or apoptosis inhibitors. Examples of feeder cells include mouse fibroblasts or human foreskin fibroblasts. Examples of differentiation inductors include Noggin or keratinocyte growth factor.

The combination of the laminin substrate with the cell culture medium of the present disclosure results in a cell culture system that can be cheaper, yet provides higher efficiency in maintaining differentiated cells. In essence, all that is required is a laminin and a minimal amount of nutrition. It is particularly contemplated that the laminin used in combination with this cell culture medium is either LN-511 or LN-521.

The cell culture system in some embodiments includes at least one of Laminin-411, Laminin-511, and Laminin-521 in the substrate, and maintains differentiated human umbilical vein endothelial cells (HUVECs) longer than shown by conventional fibronectrin substrates.

Primary Cell Transfection

The present disclosure also relates to methods for improving the transfection efficiency with primary cells (i.e. differentiated cells) and/or improving the survival rate of primary cells that have been transfected.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present disclosure, the expression of the laminin polypeptide sequence is directed by the promoter sequences of the disclosure, by operatively linking the promoter sequences of the disclosure to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the disclosure is intended to include other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the methods of the disclosure, and any such sequence may be employed, including but not limited to the SV40 and bovine growth hormone poly-A sites. Also contemplated as an element of the vector is a termination sequence, which can serve to enhance message levels and to minimize readthrough from the construct into other sequences. Additionally, expression vectors typically have selectable markers, often in the form of antibiotic resistance genes, that permit selection of cells that carry these vectors.

The primary cells can be transfected using any known transfection method. Such methods include a baculovirus, a lentivirus, lipofectamine, the calcium phosphate method, liposomes, cationic polymers, electroporation, sonoporation, optical transfection, gene electrotransfer, impalefection, hydrodynamic injection, gene gun, magnetofection, and viral transduction. The vector is selected to match with the transfection method.

The transfected primary cells are cultured upon the substrate that contains the laminin. A cell culture system generally comprises a substrate and a cell culture medium. The substrate provides a support upon which the cells can grow. The medium provides the nutrients to the cells. It is contemplated that the cell culture medium will be completely defined and xeno-free. The medium should also be devoid of any differentiation inhibitors, feeder cells, or differentiation inductors, or apoptosis inhibitors. Examples of feeder cells include mouse fibroblasts or human foreskin fibroblasts. Examples of differentiation inductors include Noggin or keratinocyte growth factor.

Normal transfection efficiency is about 10%. It is believed that a higher efficiency rate can be obtained using the substrates described herein.

The following examples are for purposes of further illustrating the present disclosure. The examples are merely illustrative and are not intended to limit devices made in accordance with the disclosure to the materials, conditions, or process parameters set forth therein.

EXAMPLES

A. HUVEC Cell Derivation

HUVECs were derived from umbilical cords according to a modified protocol disclosed in Baudin et al., A protocol for isolation and culture of human umbilical vein endothelial cells, Nat. Protoc. 2007; 2(3):481-5 (hereinafter "Baudin"). Collagenase A solution from Roche in PBS buffer was briefly injected into pre-washed vein of human umbilical cord. Collagenase was incubated at 37 degrees Celsius, and then washed away with cell suspension. The cell suspension was plated on laminin-coated plates.

AI. Laminin Coating

Primary HUVECs were cultured on top of different substrate coatings including conventional fibronectin as a control and recombinant laminins, specifically human recombinant LN-411, LN-511, LN-521, LN-111, and LN-211, either alone or in combination. Combinations of LN-411/LN-511, LN-511 alone, and LN-521 alone showed successful long-term culture of HUVEC cells in vitro.

Laminin substrate coatings were stored in PBS at −70 degrees Celsius, were thawed on wet ice (approximately 4 degrees Celsius) and then dissolved in sterile PBS to a concentration of 5 micrograms per milliliter (ug/ml). 80 microliters (uL) of substrate solution was used to coat 96-well plates overnight at 4 degrees Celsius or for 2 hours at 37 degrees Celsius in a cell culture incubator. The wells of the 96-well plates were pre-washed with PBS buffer prior to plating the cells.

AII. Culturing

HUVECs were cultured in sterile incubators, each with the temperature set to 37 degrees Celsius and $CO_2$ levels set to 5%. Sarstedt 96-cell plates were used for culturing, with an added medium amount of 200 uL/well. The medium composition used, as disclosed in Baudin, was filtered through a 0.22 micrometer (um) filter and stored at 4 degrees Celsius for about 2-3 weeks.

AIII. Cell Passaging

HUVEC cells were passaged in vitro at several densities. HUVEC cells were split into 1:5, 1:10, or 1:20 splits using standard Trypsin-EDTA solution from Gibco. Trypsin-EDTA was applied pre-warmed for about 3-5 minutes. Trypsin was inhibited by serum within the cell culture medium.

AIV. HUVEC Cell Analysis

HUVECs were first characterized by quantification methods. This included recorded and quantifying HUVECs using the Operetta machine from Perkin-Elmer. Magnification was chosen at 10×, 20×, and 40×.

Immunocytochemistry analysis was subsequently performed on HUVECs by pre-washing adherent cells twice with warm PBS buffer, applying 100 uL of 4% paraformaldehyde (PFA) solution, incubating at room temperature for 20 minutes, then washing the wells three times with PBS. Fixed cells were permeabilized by 0.1% A Triton-X solution at room temperature for 15 minutes, then washed by PBS buffer three times and blocked by 10% bovine fetal serum in PBS, supplemented by 0.1% Tween stored for 30 minutes at room temperature or overnight at 4 Celsius.

HUVECs typically express the endothelial marker known as von Willebrand factor (vWF) after 4 passages. Therefore, vWF factor was used to define positive cells belonging to the endothelial cell type. Smooth Muscle Actin (SMA) was used as a negative marker to define fibroblasts or fibroblast-like differentiated cells within in vitro population. DAPI was used to stain the nuclei, which is necessary to define Total Cell Population using cell population analysis on the Operetta machine using Harmony software provided by Perkin-Elmer. Rhodamine-phalloidine conjugates were used to visualize f-actin, which acts as a marker of cytoskeleton structure and cell borders.

Quantitative RT-PCR was performed to compare quantitative levels of positive marker (vWF factor) versus negative marker (SMA) in HUVEC cultures in vitro after long passaging.

Figure 3:
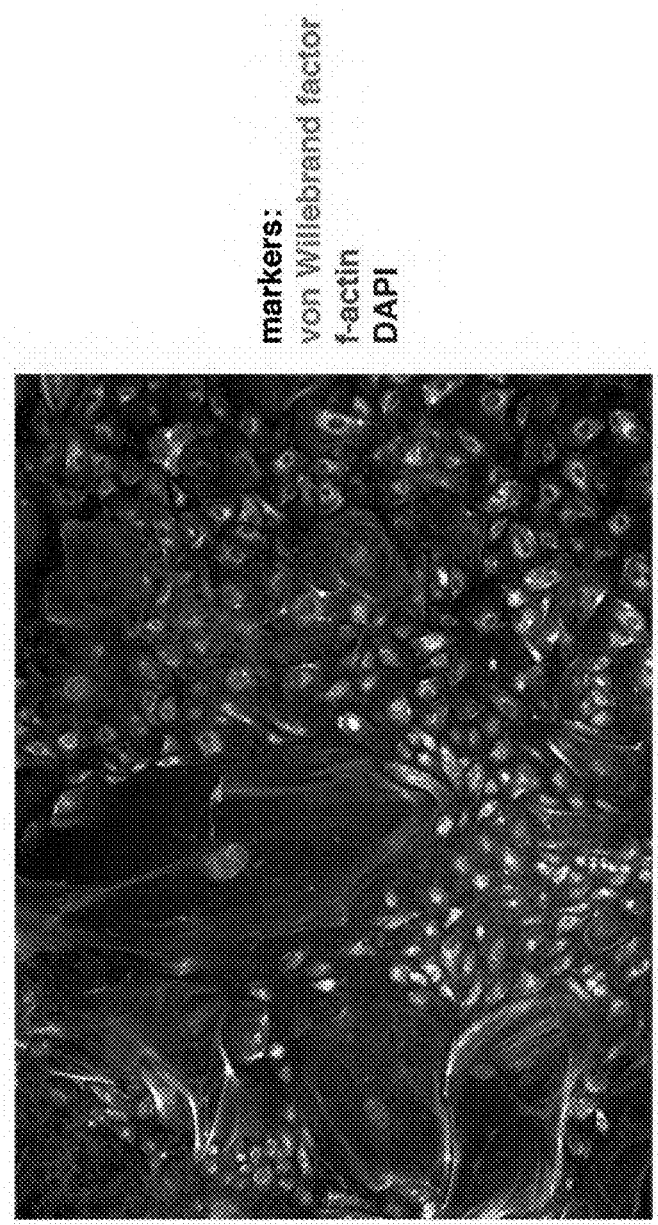
FIG. 3 is a photomicrograph of human umbilical vein endothelial cells (HUVECs) grown on a fibronectin (FNE) substrate, 10× magnification, after 5 passages, with expression of von Willebrand factor (vWF), f-actin, and DAPI.
Figure 4:
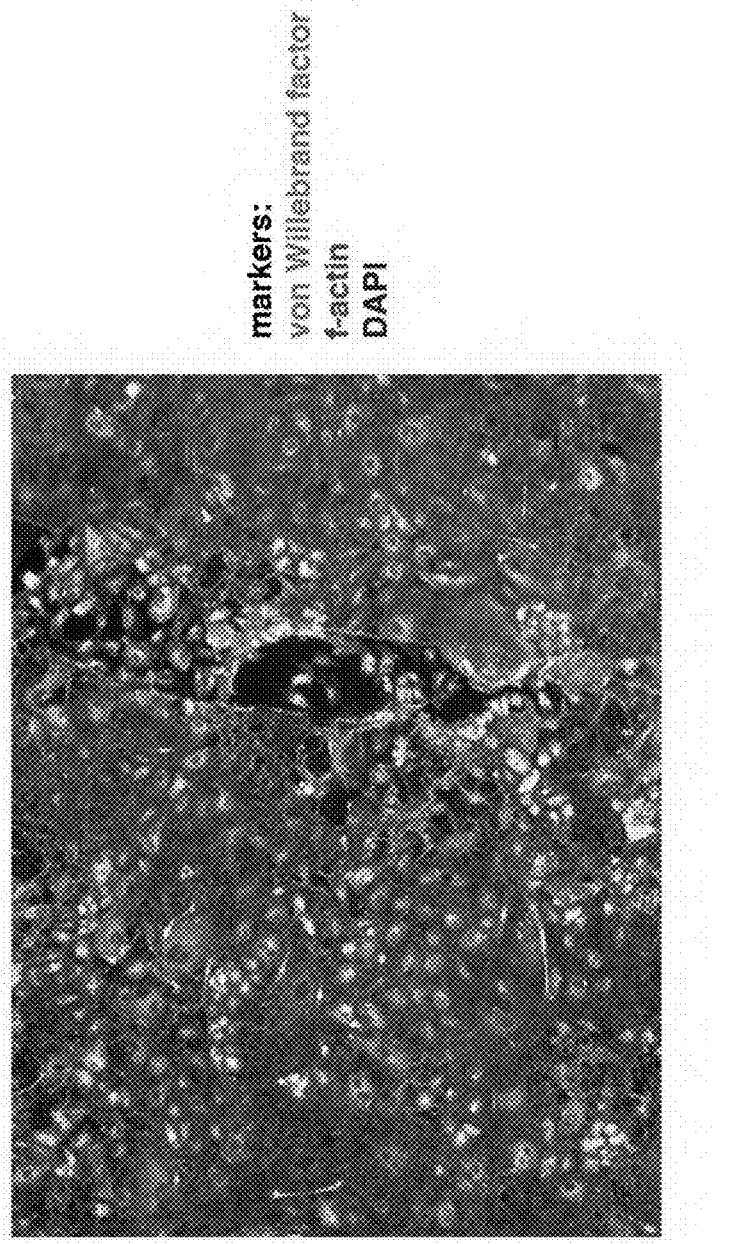
FIG. 4 is a photomicrograph of HUVECs grown on a LN-521 substrate, 10× magnification, after 5 passages, with expression of vWF, f-actin, and DAPI.
Figure 5:
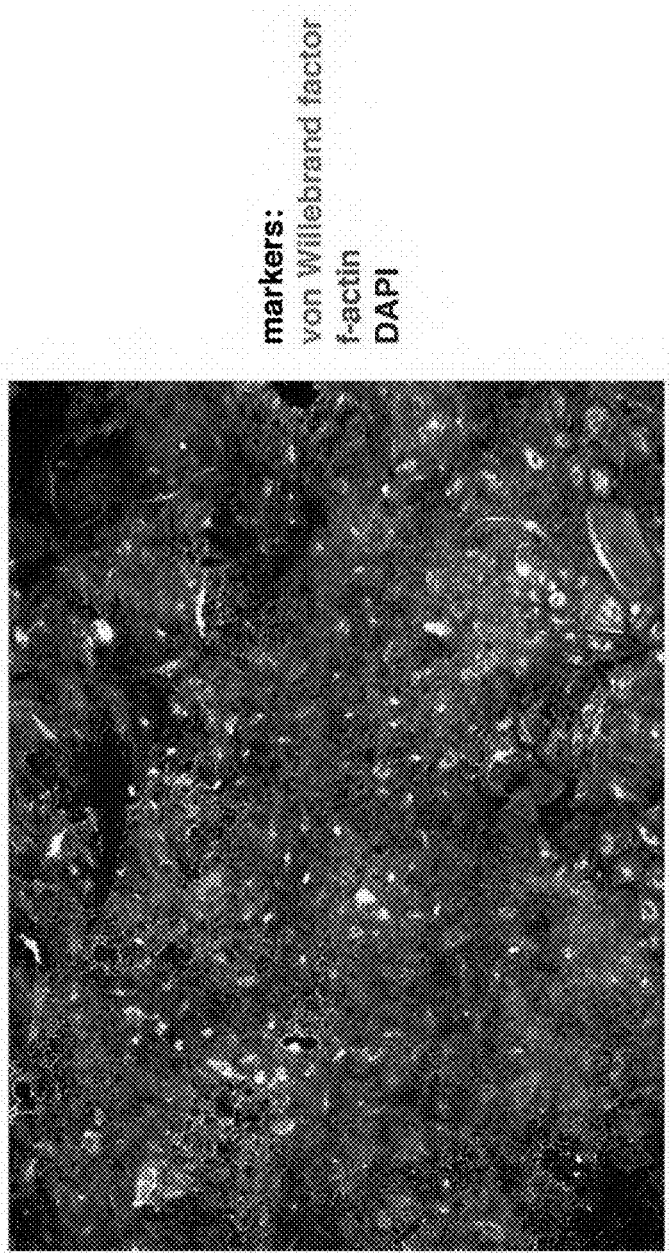
FIG. 5 is a photomicrograph of HUVECs grown on a LN-521 substrate, 10× magnification, after 7 passages, with expression of vWF, f-actin, and DAPI.

FIG. 3 is photomicrograph of human umbilical vein endothelial cells (HUVECs) grown on a fibronectin (FNE) substrate, 10× magnification, after 5 passages, with expression of von Willebrand factor (vWF), f-actin, and DAPI. FIG. 4 is a photomicrograph of HUVECs grown on a LN-521 substrate, 10× magnification, after 5 passages, with expression of vWF, f-actin, and DAPI. FIG. 5 is a photomicrograph of HUVECs grown on a LN-521 substrate, 10× magnification, after 7 passages, with expression of vWF, f-actin, and DAPI. In these three figures, the von Willebrands factor (vWF) is stained and appears as a green color. As seen here, the HUVECs grown on fibronectin substrate (FIG. 3) do not express the endothelial marker as well as cells on grown on LN-521 substrate (FIG. 4 and FIG. 5), as seen by more green color expression of vWF factor. FIG. 3 has much more black, yellow, and blue color compared to FIG. 4 and FIG. 5, which are almost completely green. These figures show that LN-521 effectively prevents dedifferentiation better than conventional fibronectin substrate. The endothelial cells grow equally well on the fibronectin substrate, but do not maintain their phenotype as well.

Figure 6:
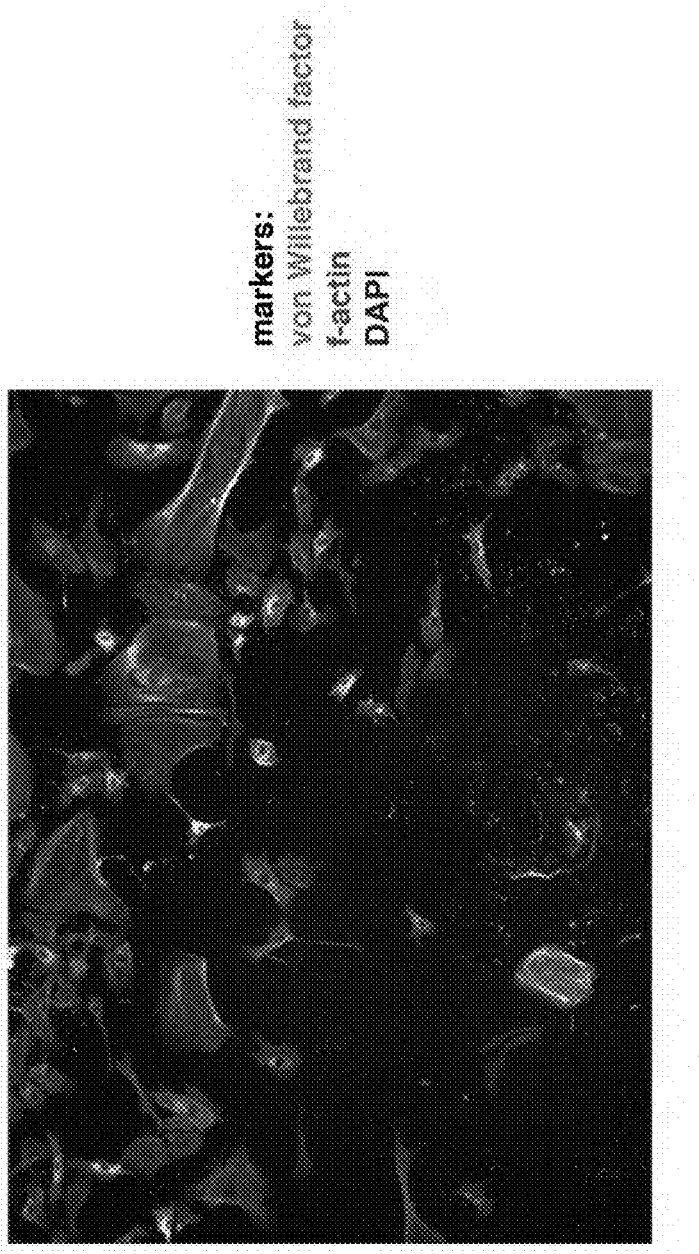
FIG. 6 is a photomicrograph of HUVECs grown on a LN-411/511 substrate, 10× magnification, after 5 passages, with expression of vWF, f-actin, and DAPI.
Figure 7:
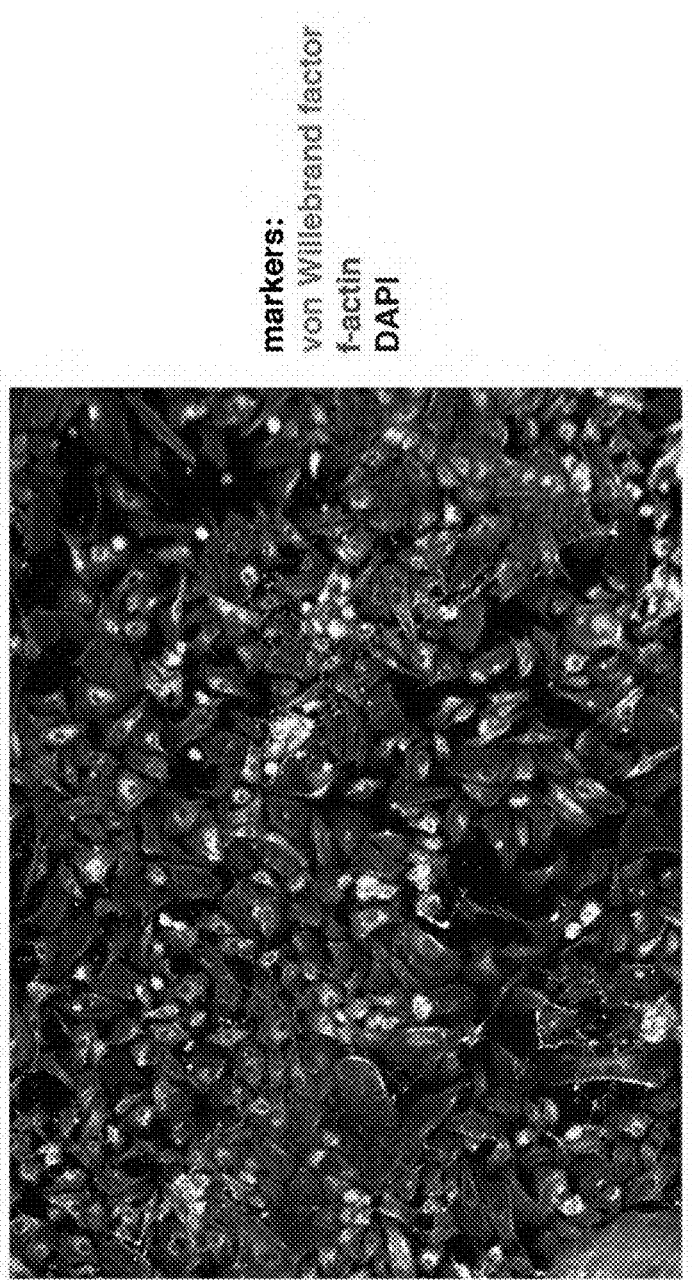
FIG. 7 is a photomicrograph of HUVECs grown on a LN-511 substrate, 10× magnification, after 5 passages, with expression of vWF, f-actin, and DAPI.

FIG. 6 is a photomicrograph of HUVECs grown on a LN-411/511 substrate, 10× magnification, after 5 passages, with expression of vWF, f-actin, and DAPI. FIG. 7 is a photomicrograph of HUVECs grown on a LN-511 substrate, 10× magnification, after 5 passages, with expression of vWF, f-actin, and DAPI. The vWF factor shows greater expression in cells grown on LN-511 relative to cells grown on LN-411/511 substrate. In FIG. 6, the majority of the picture is black or yellow. In FIG. 7, there are many more cells and each cell has some green color. However, both FIG. 6 and FIG. 7 show less vWF expression than seen for cells on LN-521 substrate in FIG. 4 and FIG. 5.

Figure 8:
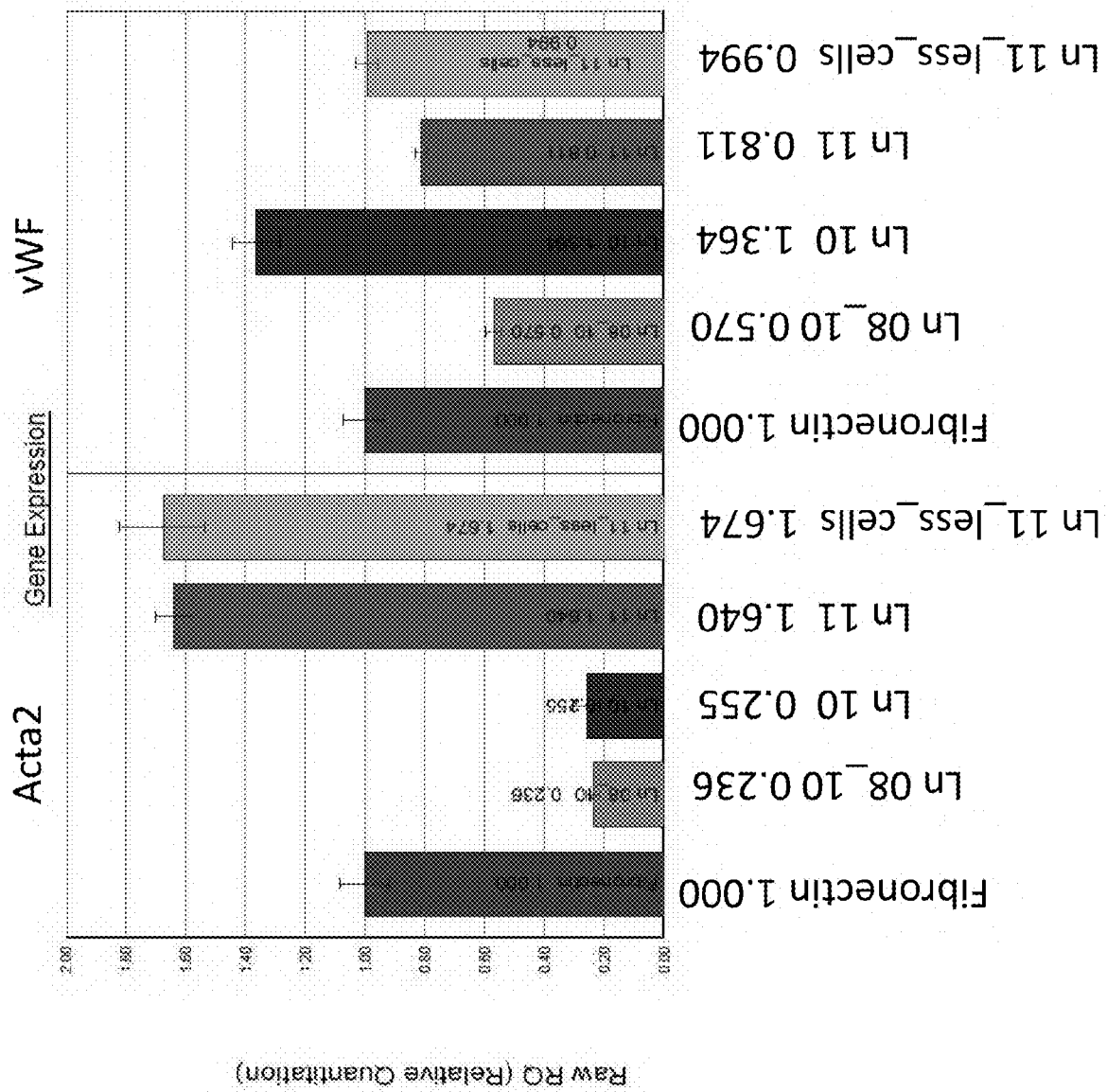
FIG. 8 is graph of RNA Gene Expression showing relatively low Acta2 gene expression (negative marker) (the five leftmost columns) and high vWF gene expression (positive marker) (the five rightmost columns) relative to a control (Fibronectin) when cells are grown on a LN-511 substrate.

FIG. 8 is graph of RNA Gene Expression showing Acta2 gene expression (negative marker) and vWF gene expression (positive marker). The data was obtained by performing qRT-PCR according to standard procedures. The Acta2 data is on the left side. The five columns are labeled, going from left to right, according to the table below. Note that Ln 08 refers to laminin-411, Ln 10 refers to laminin-511, and Ln 11 refers to laminin-521. Ln 08_10 is a mixture of laminin-411/511.

| Column | Text | Value |
| --- | --- | --- |
| Left red | Fibronectin | 1.000 |
| Left green | Ln 08_10 | 0.236 |
| Left blue | Ln 10 | 0.255 |
| Right red | Ln 11 | 1.640 |
| Right green | Ln 11_less_cells | 1.674 |

The vWF data is on the right side of FIG. 8. The five columns are labeled, going from left to right, according to the table below.

| Column | Text | Value |
| --- | --- | --- |
| Left red | Fibronectin | 1.000 |
| Left green | Ln 08_10 | 0.570 |
| Left blue | Ln 10 | 1.364 |
| Right red | Ln 11 | 0.811 |
| Right green | Ln 11_less_cells | 0.994 |

Figure 9:
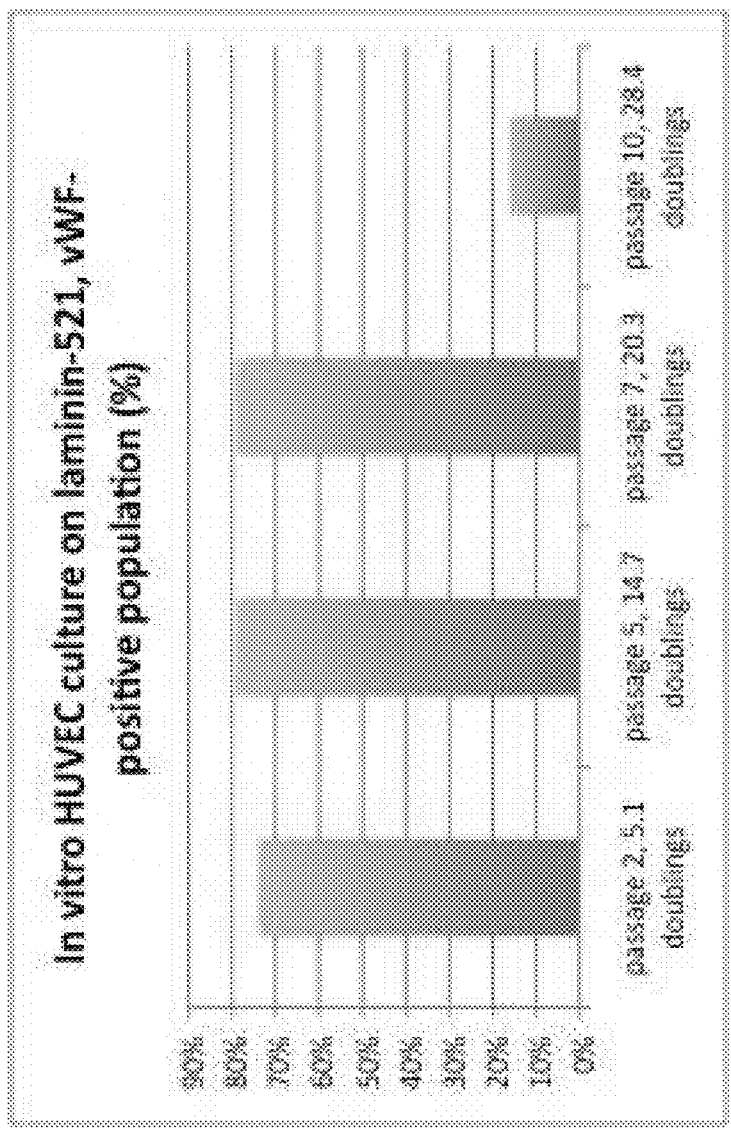
FIG. 9 is a graph of quantified percentage of vWF-positive HUVECs within a population after a long-term culture of HUVECs on human recombinant laminin-521.
Figure 10:
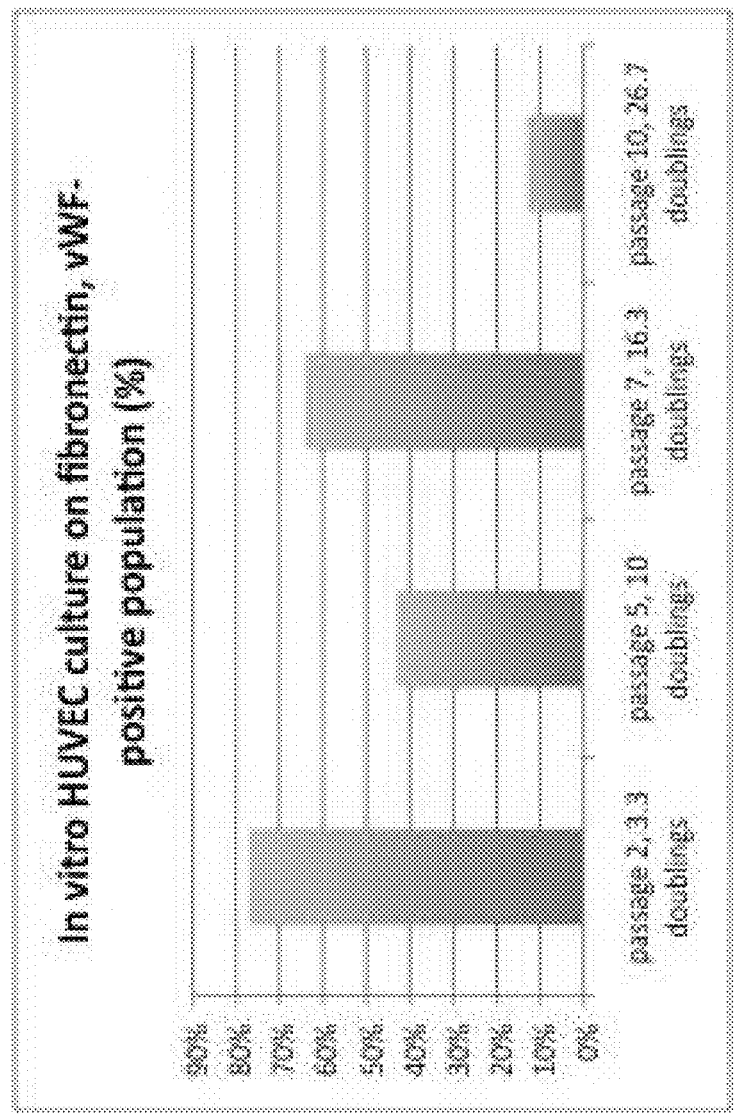
FIG. 10 is graph of quantified percentage of vWF-positive HUVECs within a population after a long-term culture of HUVECs on human recombinant Fibronectin.

FIG. 9 is a graph of quantified percentage of vWF-positive HUVECs within a population after a long-term culture of HUVECs on human recombinant laminin-521. FIG. 10 is a graph of quantified percentage of vWF-positive HUVECs within a population after a long-term culture of HUVECs on human recombinant Fibronectin. With reference to FIG. 9 and FIG. 10, the percentage of vWF-positive HUVECs is stable after 7 passages (approximately 20.3 doublings) when Laminin-521 is used as the substrate. By contrast, the percentage of vWF-positive HUVECs is not stable at 5 and 7 passages when traditional fibronectin is used as the substrate. Therefore, recombinant LN-521 substrate enables HUVECs to retain their phenotype longer than when plated on fibronectin substrate.

Figure 11:
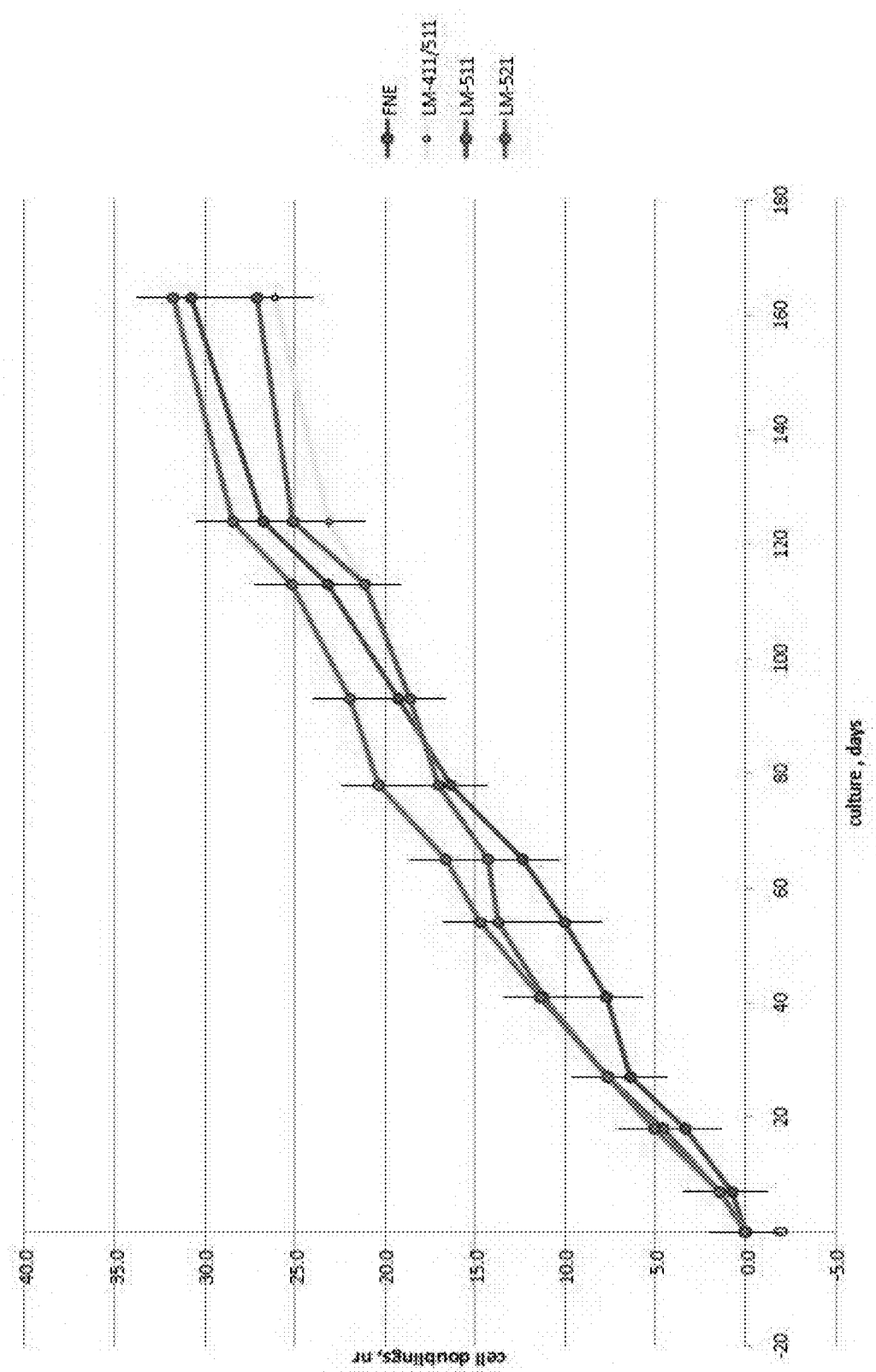
FIG. 11 is proliferation curve showing the proliferation of HUVECs on different substrate coatings, dependent of days in culture. The LN-521 line always has the greatest value. The LN-411/511 and LN-511 lines essentially overlap until −115 days, at which point the LN-511 line is greater. The FNE line has the lowest value until −80 days, when it then crosses over to have the second-highest value.

FIG. 11 is a proliferation curve showing the proliferation of HUVECs on different substrate coatings, dependent on days in culture up through 160 days. LN-521 always had the highest number of doublings. LN-511 and LN-411/511 also supported a high number of doublings up to around 65 days in culture. Around that time, their advantage over fibronectin (FNE) began to shrink.

B. Mouse Pancreatic Insulin-Producing Islet Beta Cell Derivation

Murine islet cells were derived according to the modified protocol by Dong-Sheng Li et. al., as published in "A protocol for islet isolation from mouse pancreas," Nature Biotechnology 2009. All manipulation with mouse pancreas was performed under a dissection microscope, with a corresponding magnification of 0.63. All instruments in contact with mouse pancreas were sterilized with ethanol solution. The bile pathway to the duodenum in mouse subjects was blocked by clamping ampula with surgical clamps.

A 30 gauge, one-half inch needle, was inserted into the joint site of hepatic duct and cystic duct and inserted until reaching the middle of common bile duct. Collagenase A (available from Roche) was used at a concentration of 5 mg/ml. Collegenase A was slowly injected into murine pancreas up to volume of 3 ml and thereby inflating the pancreas. Inflated pancreas was removed and soaked in 2 ml of collagenase A solution. Pancreas in collagenase A solution was transferred to sterile 50 ml Falcon tube, incubated at temperature of 37° C. in water bath, and shaken every 5 minutes for better spreading of collagenase. After 18-25 minutes of incubation in water bath, the pancreas was substantially dissociated.

Digestion was terminated by putting the tube on ice and adding 25 ml of ice cold buffer. In order to remove exocrine cells and collagenase solution, the islet cells were repeatedly washed and centrifuged. The resulting suspension of cells was centrifuged at 290 g for 30 seconds at 4° C. and supernatant was discarded. The remaining pellet was resuspended with 20 ml ice-cold buffer, centrifuged again at 290 g for 30 seconds at 4° C., and the supernatant was discarded. The resulting pellet was resuspended with 15 ml of buffer and poured onto a prewetted 70 micrometer (µm) cell strainer. The tube was washed with 20 ml of buffer and poured again onto the strainer. Islet cells from the strainer were rinsed with islet culture medium into a 100-mm tissue culture Petri dish. Lastly, the islet cells were hand-picked and transferred to another 100-mm Petri dish.

BI. Islet Beta Cell Depletion

In order to completely remove the remains of exocrine tissue and non-islet connective tissue from islet culture, the islet beta cells were cultured for 2-3 days in 100-mm Petri dish, which allowed the cells and cell aggregates to settle. After that the islets were evaluated for having a smooth, round shape that was free from debris. Selected islets were hand-picked and plated onto another 100-mm Petri dish.

BII. Transferring Mouse Islets onto Recombinant Human Laminin-Coated Tissue Culture-Grade Plates Tissue-culture grade 96-well plates, e.g. available from Perkin-Elmer Cell Carrier plates or Sarstedt, were coated with solutions of human recombinant laminins suspended in PBS solution for over 2 hours at 37 C (stored in cell incubator) or for over 20 hours at 4 C. 96-well plates were washed 2-3 times with PBS buffer before use. Islet culture medium was input into the wells prior to islet plating, and was then equilibrated in an incubator. Islet cells were hand-picked and plated onto laminin-coated plates. Culture medium was changed every 2-3 days.

BIII. Analysis of Islet Beta Cells

Figure 19:
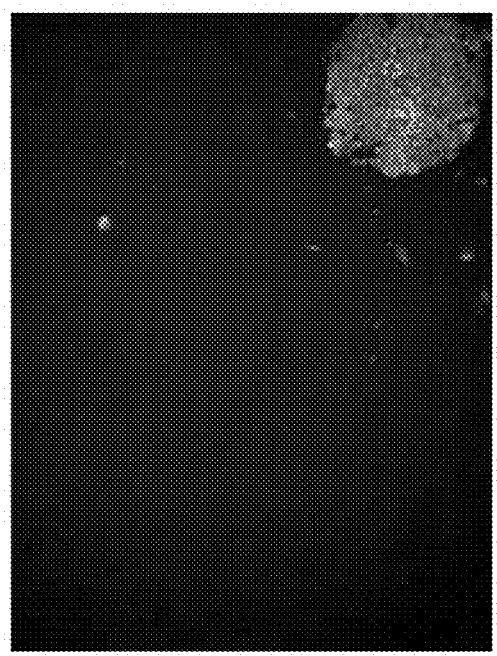
FIG. 19 is a phase-contrast micrograph of mouse pancreatic insulin-producing islet beta cells plated on a surface coated with human recombinant LN-521 for 3-4 weeks at 10× magnification and subsequently (a) stained positively for C-peptide (green) and (b) stained positively for C-peptide (green) and Hoechst (blue).
Figure 19:
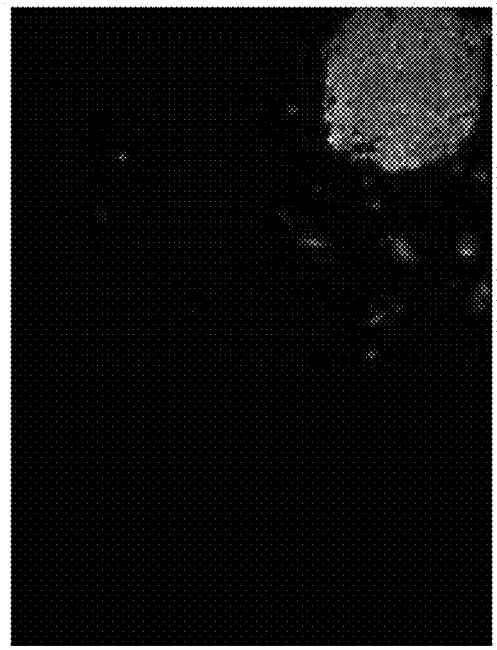
Figure 20:
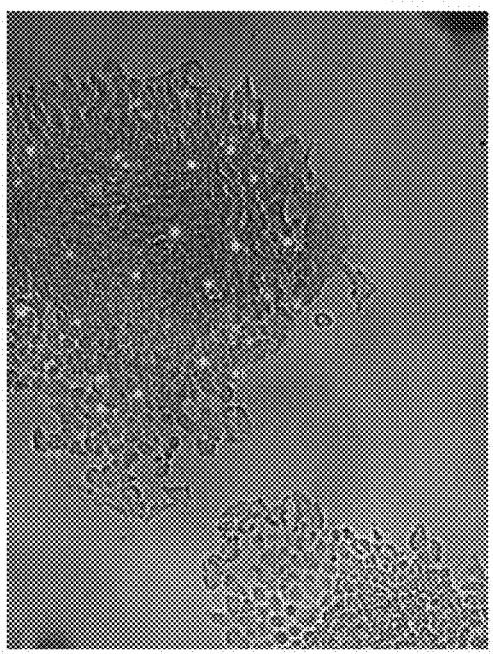
FIG. 20 is a phase-contrast micrograph of mouse pancreatic insulin-producing islet beta cells plated on a surface coated with human recombinant LN-521 for 3-4 weeks at 20× magnification and subsequently (a) stained positively for EdU (green) in nuclei of proliferated cells and (b) stained positively for Edu (green) co-localized with phase contrast photograph of islet.
Figure 20:
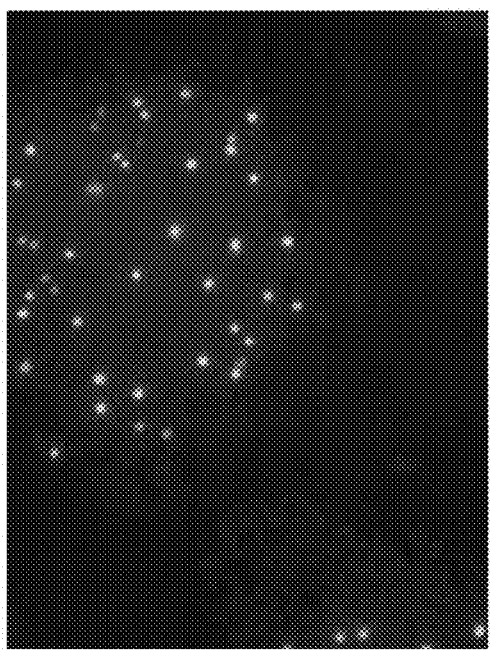
Figure 21:
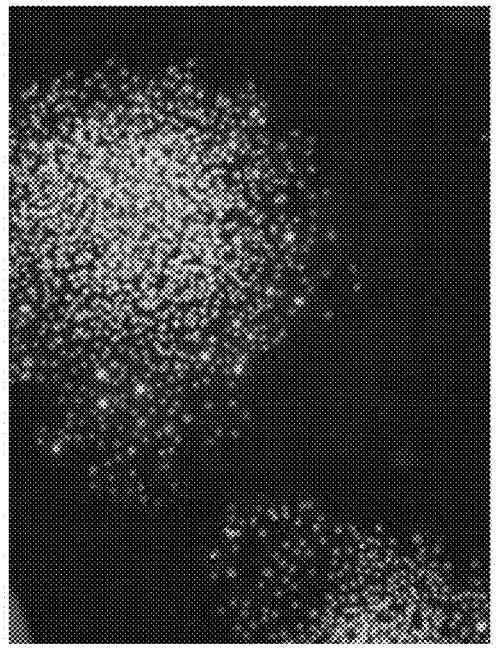
FIG. 21 is a phase-contrast micrograph of mouse pancreatic insulin-producing islet beta cells plated on a surface coated with human recombinant LN-521 for 3-4 weeks at 20× magnification and subsequently (a) stained positively for EdU (green) in nuclei of proliferated cells and (b) stained positively for Edu (green) co-localized with Hoechst (blue).
Figure 21:
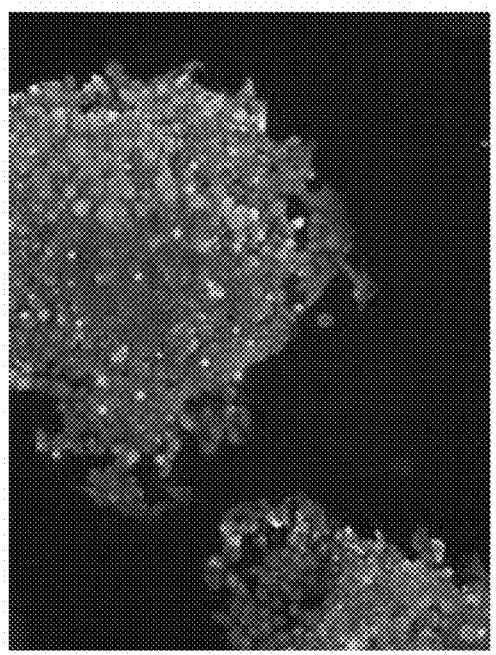

Islet cells were analyzed according to three different methodologies. FIGS. 12-18 pertain to analysis of beta cell morphology, which includes the use of a phase-contrast microscope at magnification of ×4, ×10, ×20 and ×40. FIG. 19 pertains to analysis of beta cell immunohistochemistry, specifically involving an antibody against C-peptide, a marker of insulin expression. FIG. 20-21 pertains to analysis of cell proliferation by EdU staining. The EdU molecule incorporates into DNA strands of nuclei of cells that have divided. Rhodamine-phalloidine, used for cytoskeleton structure analysis, and Hoechst, used to stain the nuclei of cells, were also used in combination with anti-C-peptide and/or EdU for additional information.

Mouse islets were cultured on human recombinant laminins in order to imitate the natural "environmental niche" for beta cells and to enable the beta cells to grow as a syncytium. When α5 chain laminins were used as coatings in vitro, beta cells were able to express insulin genes. The result was that different types of laminins exerted different effects on mouse pancreatic islets, e.g. the ability to produce insulin or proliferate.

Figure 12:
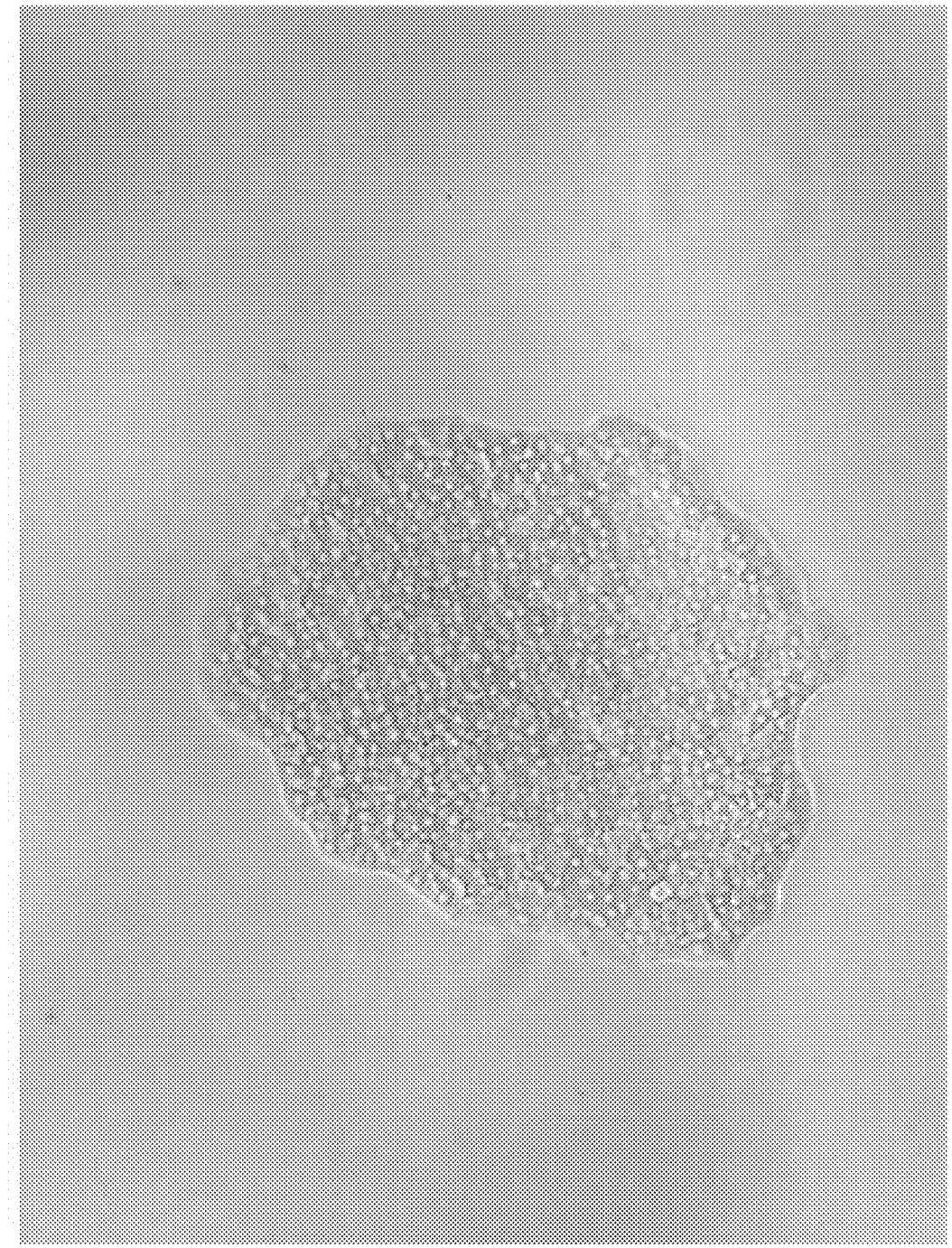
FIG. 12 is a phase-contrast micrograph of mouse pancreatic insulin-producing islet beta cells plated on a surface coated with LN-521, 10× magnification, 3 week culture.
Figure 13:
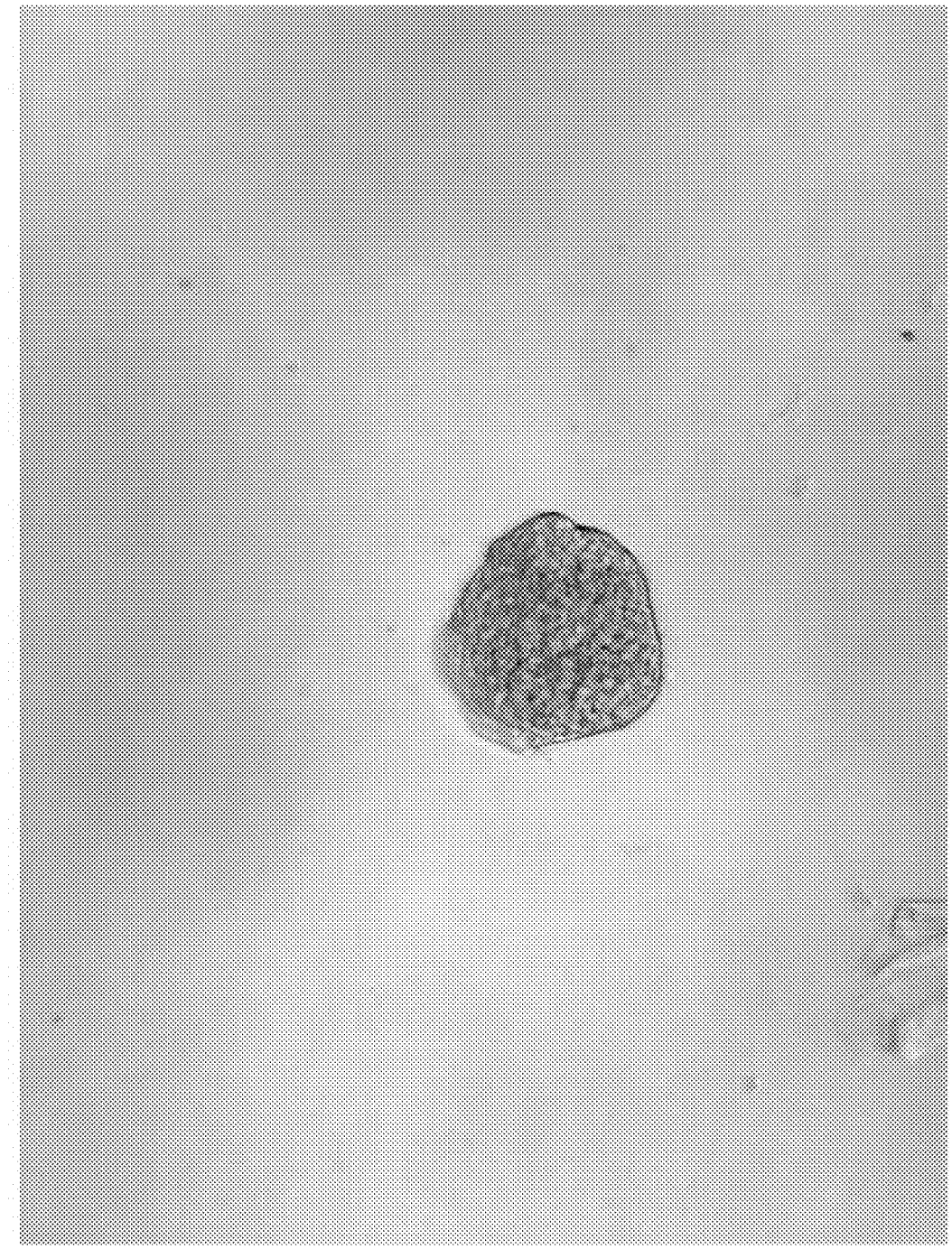
FIG. 13 is a phase-contrast micrograph of mouse pancreatic insulin-producing islet beta cells plated on an uncoated surface, 10× magnification, 3 week culture.
Figure 14:
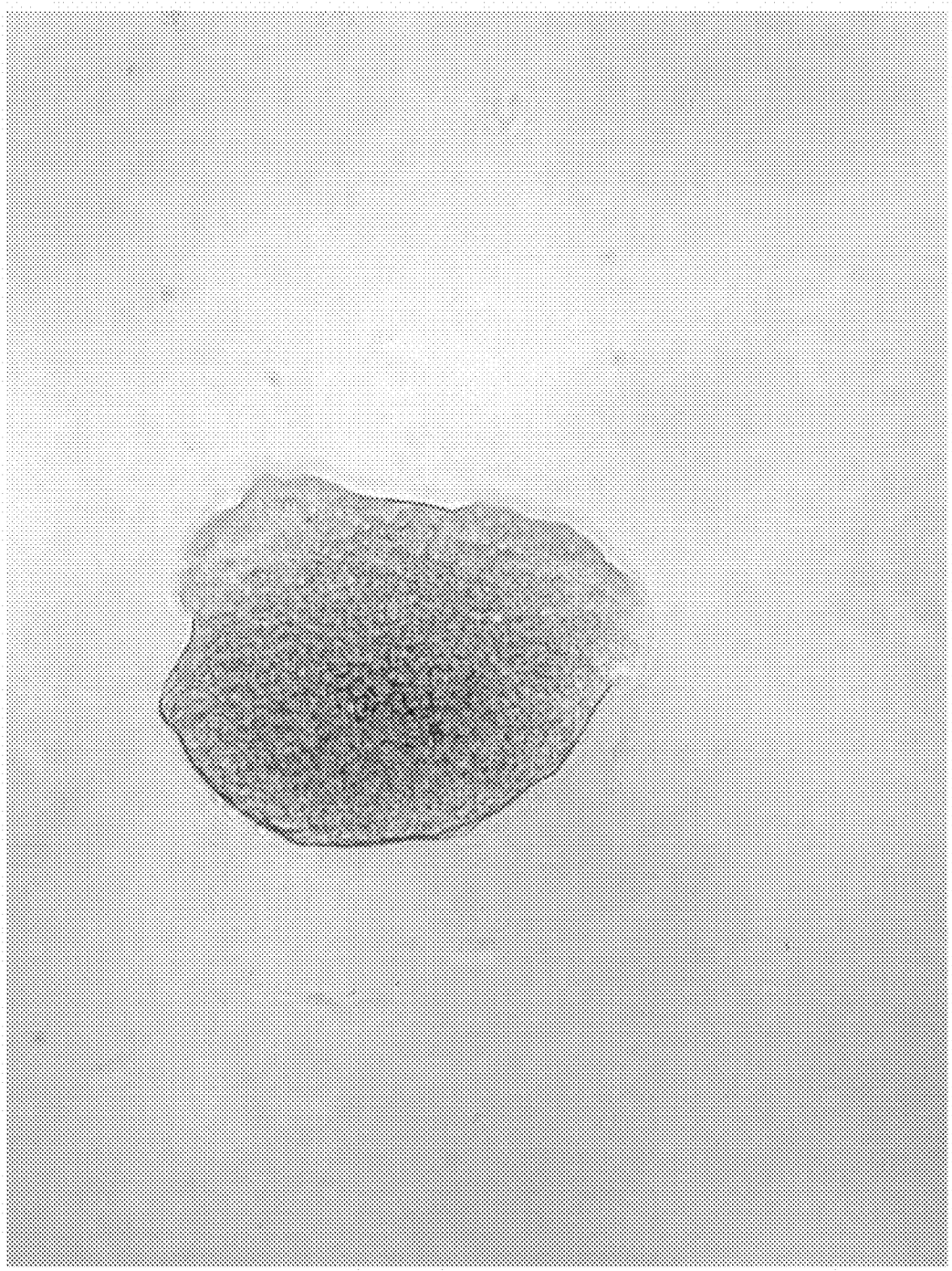
FIG. 14 is a phase-contrast micrograph of mouse pancreatic insulin-producing islet beta cells plated on a surface coated with LN-411, 10× magnification, 3 week culture.
Figure 15:
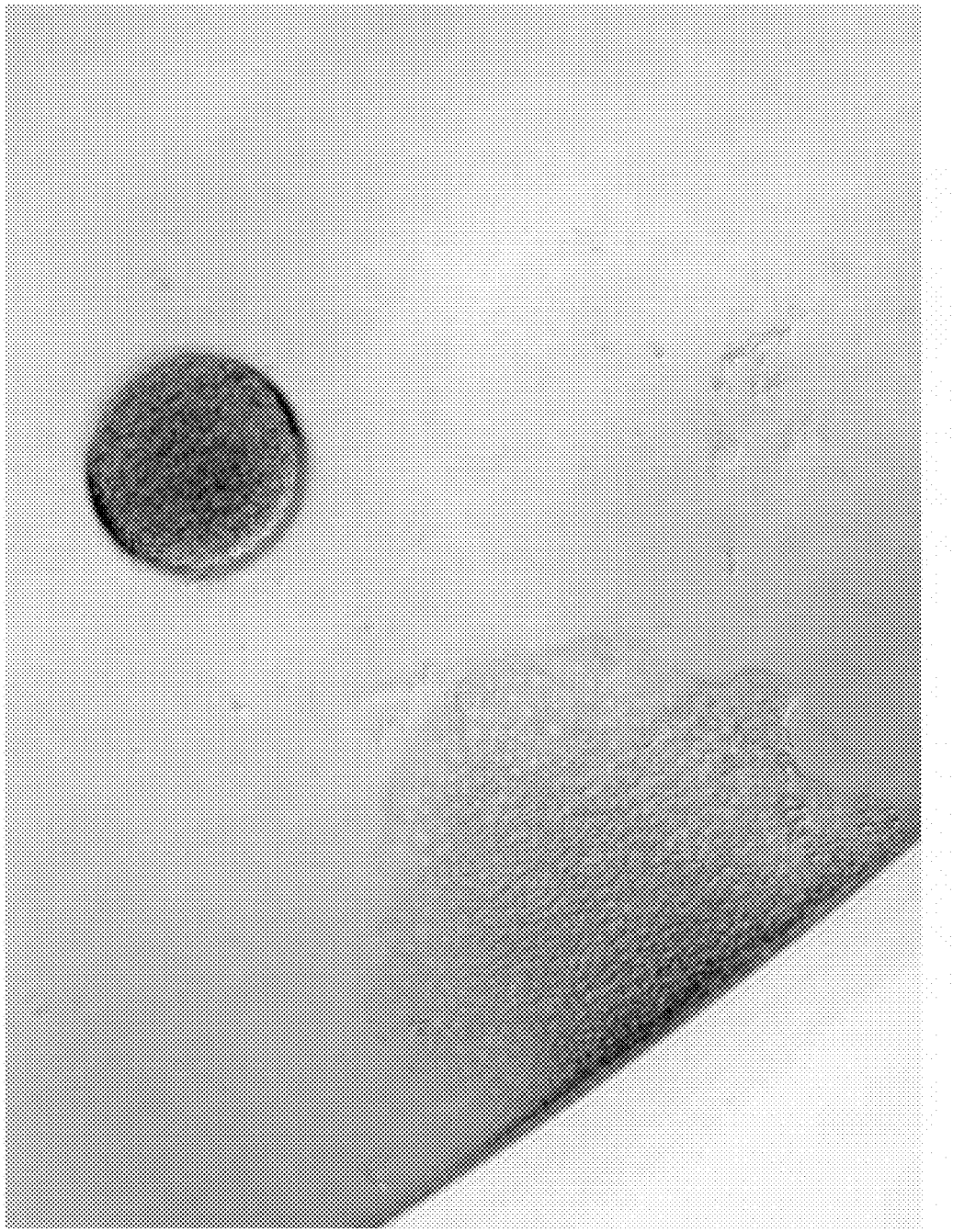
FIG. 15 is a phase-contrast micrograph of mouse pancreatic insulin-producing islet beta cells plated on a surface coated with LN-511, 10× magnification, 3 week culture.
Figure 16:
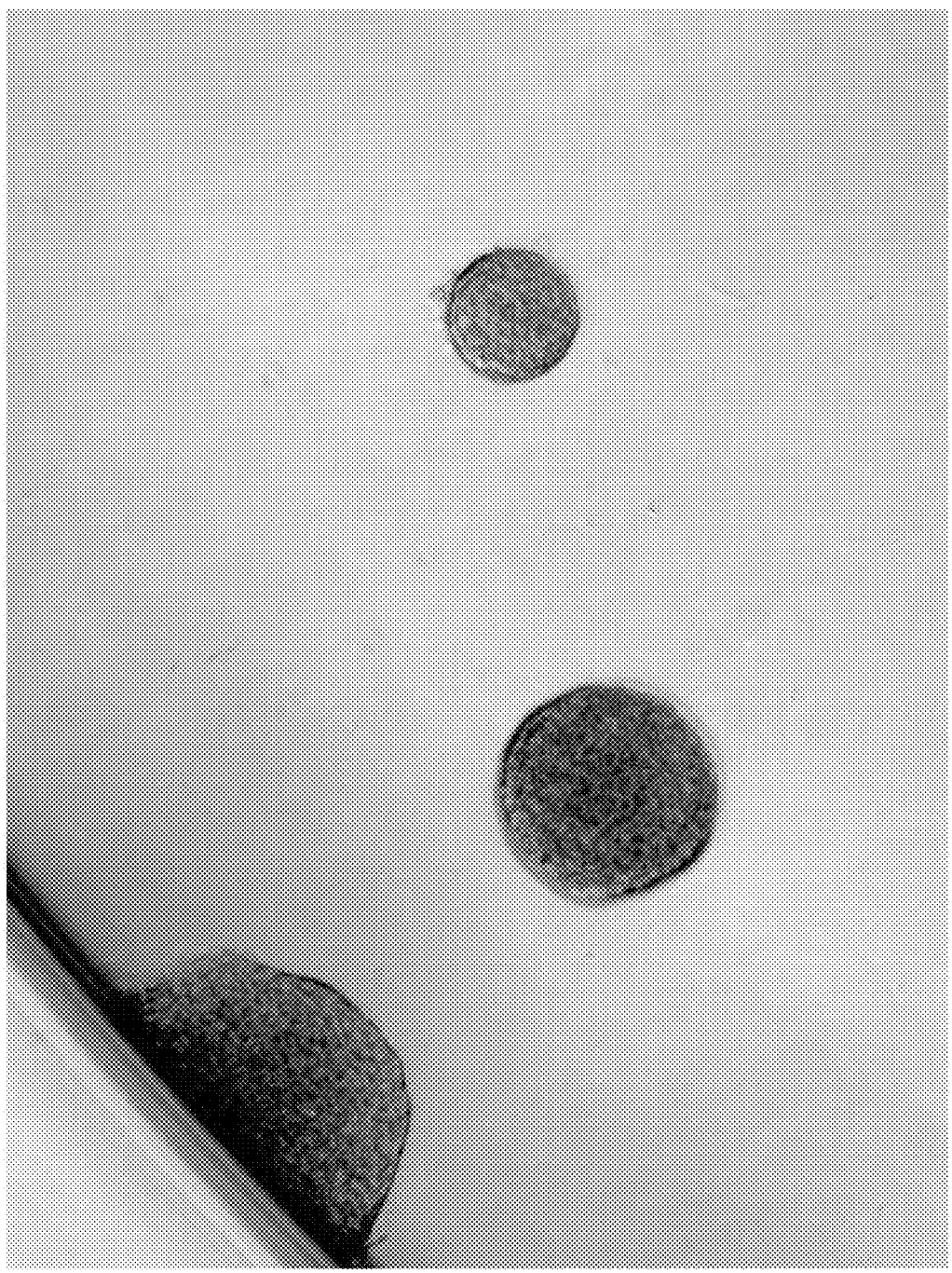
FIG. 16 is a phase-contrast micrograph of mouse pancreatic insulin-producing islet beta cells plated on a surface coated with LN-111, 10× magnification, 3 week culture.

Laminins 411, 511, 111, and 521 were coated on a surface before depositing islets. FIGS. 12-16 show the results. FIG. 12 shows the islets on a surface coated with LN-521. FIG. 13 shows the islets on an uncoated surface. FIG. 14 shows the islets on a surface coated with LN-411. FIG. 15 shows the islets on a surface coated with LN-511. FIG. 16 shows the islets on a surface coated with LN-111. Desirably, the islet would adhere and spread to the surface.

As seen in FIG. 12, LN-521 provided a robust, long-lasting effect of islet adhering uniformly and spreading upon the culture plate surface. The islet of FIG. 13 did not adhere well on an uncoated surface, as seen in its generally circular shape. With reference to FIG. 14, the islet plated on LN-411 did not have a uniform shape of adhesion. The right side adhered, but the left side failed to adhere. With reference to FIG. 15, the islets plated on LN-511 had different behavior, or in other words were inconsistent. One islet adhered, while one did not. Looking at FIG. 16, the islets plated on LN-111 failed to adhere and spread. The effect of LN-521 on islets may be due to a specific molecule interaction or characteristic.

Figure 17:
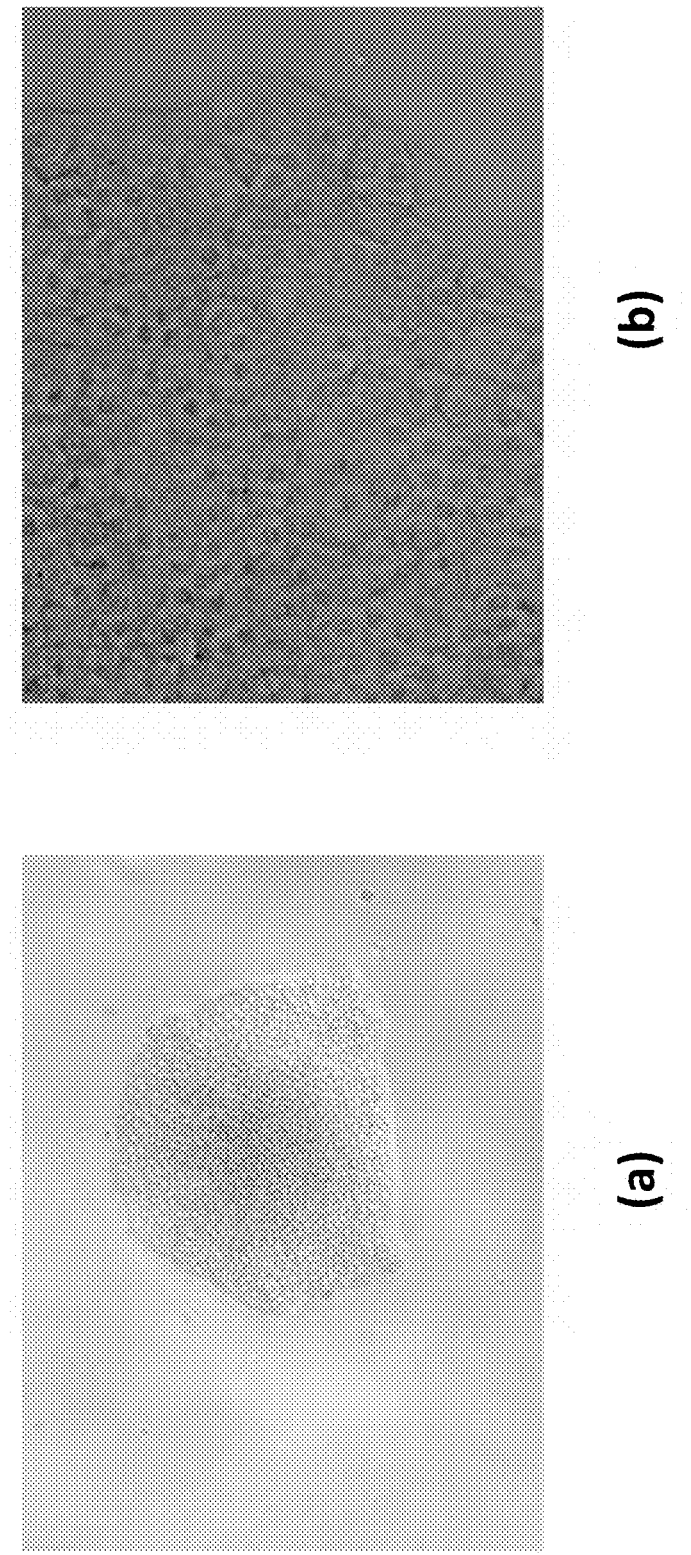
FIG. 17 is a phase-contrast micrograph of mouse pancreatic insulin-producing islet beta cells plated on a surface coated with human recombinant LN-521 at (a) 10× magnification and (b) 40× magnification.
Figure 18:
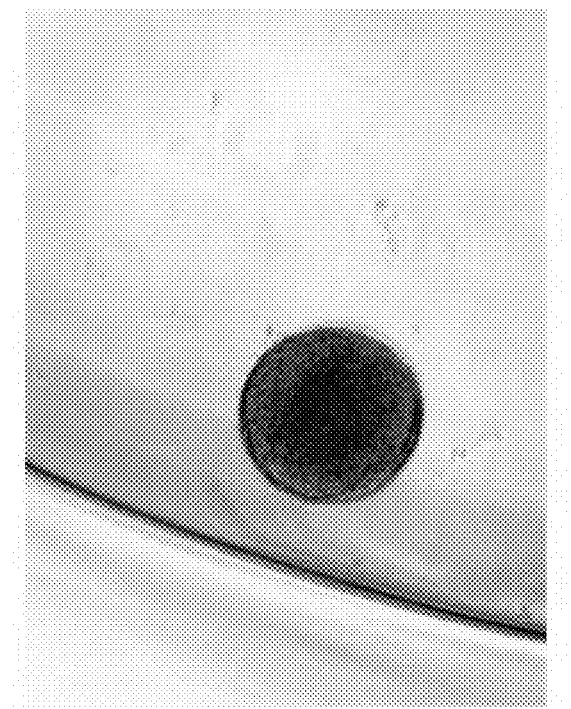
FIG. 18 is a phase-contrast micrograph of mouse pancreatic insulin-producing islet beta cells plated on a surface coated with human recombinant LN-111 at (a) 10× magnification and (b) 40× magnification.
Figure 18:
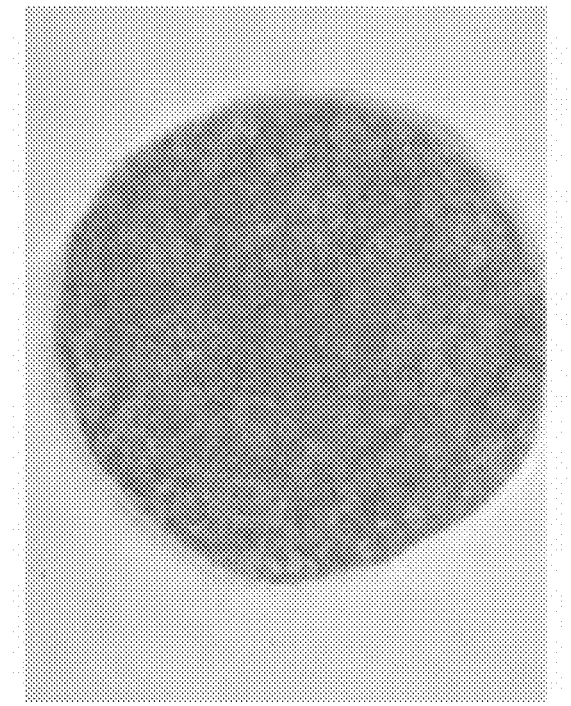

With reference to FIGS. 17-18, a specific effect on the morphology of the islets is demonstrated by comparing islets deposited upon laminin-521 in FIG. 17 to islets deposited upon laminin-111 in FIG. 18. Mouse pancreatic insulin-producing beta islets expanded on human recombinant laminin-521, whereas islets expanded on laminin-111 retained their three-dimensional spherical shape. Differences in morphology and in the cell community infrastructure can be seen on either low magnification (×10) (FIGS. 17(a) and 18(a)) or high magnification (×40) (FIGS. 17(b) and 18(b)).

With reference to FIG. 19, after 3-4 weeks in culture, beta islets were deposited upon laminin-521 and stained positively for C-peptide, which is a marker for insulin expression. FIG. 19(a) shows a positive indication of C-peptide, and therefore successful production of insulin, when beta islets are deposited on laminin-521. FIG. 19(b) shows the positive indication of C-peptide, as well as the nucleus of beta islets on laminin-521, shown through blue colored Hoechst indicator (the upper right dot).

With reference to FIG. 20, after 3-4 weeks in culture, beta islets deposited on laminin-521 maintained capacity for proliferation. With reference to FIG. 20(a), beta islets demonstrated positive EdU staining, shown by a green color (the solid dots) in the nuclei of proliferated cells. The nuclei are spread out relative to the beta islets in FIG. 19. In FIG. 20(b), the green color EdU stain was merged with a phase-contrast photograph for additional context on the location of proliferated nuclei.

In FIG. 21, the joint effect of proliferation of islets cultured upon laminin-521 and expression of C-peptide within the same islets is demonstrated. With reference to FIG. 21(a), mouse pancreatic insulin-producing beta islet cells when cultured on human recombinant laminin-521 maintained proliferation potential and expressed C-peptide. This was demonstrated by the contemporaneous positive green EdU staining as well as the orange color (indication of c-peptide, marker of insulation production) in FIG. 21(a). The green EdU stains were the sharp bright points, while the orange color was the portions surrounding the sharp points. In FIG. 21(b), blue Hoechst dye was localized in the nuclei of all islets, while green EdU indicated the nuclei of islets divided during the last three days. The islets in FIG. 21(b) that have divided during the last three days are farther spaced apart than the nuclei of all islet cells shown by Hoechst. The blue nuclei were the extremely bright spots, while the green nuclei were the less bright spots around the perimeter.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for maintaining the phenotype of a differentiated cell in a cell culture, comprising:
providing a cell culture substrate as a layer on a surface, the layer comprising a laminin, wherein the laminin is an intact protein or a protein fragment;
plating the differentiated cell directly on the cell culture substrate; and
culturing the plated differentiated cell on the layer in a xeno-free and chemically defined cell culture medium, wherein the cell culture medium has a human serum albumin concentration of at least 0.3 mM;
whereby the phenotype of the differentiated cell is maintained in the cell culture;
wherein the laminin is laminin-521 and/or laminin-511, and wherein the differentiated cell is a keratinocyte.

2. The method according to claim 1, wherein the keratinocyte is a primary keratinocyte.

3. The method according to claim 1, wherein the laminin is laminin-521.

4. The method according to claim 1, wherein the laminin is laminin-511.

5. The method according to claim 1, wherein the laminin is an effective recombinant laminin.

6. The method according to claim 1, wherein the cell culture substrate consists of the laminin and a cadherin.

7. The method according to claim 1, wherein the cell culture substrate consists of the laminin(s).

8. The method according to claim 1, wherein the phenotype is maintained for at least 3 weeks in culture.

9. The method according to claim 1, wherein the cell culture medium does not contain any differentiation inhibitors, differentiation inductors, or apoptosis inhibitors.

10. The method according to claim 1, wherein the laminin is an intact protein.

11. The method according to claim 1, wherein the cell culture medium does not contain any feeder cells.

12. The method according to claim 1, wherein the cell culture does not contain any feeder cells.

13. A method for maintaining the phenotype of a differentiated cell in a cell culture, comprising:
providing a xeno-free and chemically defined cell culture substrate as a layer on a surface, the layer comprising a laminin, wherein the laminin is an intact protein or a protein fragment;
plating the differentiated cell directly on the cell culture substrate; and
culturing the plated differentiated cell on the layer in a xeno-free and chemically defined cell culture medium;
whereby the phenotype of the differentiated cell is maintained in the cell culture;
wherein the laminin is laminin-521 and/or laminin-511, and wherein the differentiated cell is a hepatocyte.

14. The method according to claim 13, wherein the cell culture medium does not contain any differentiation inhibitors, feeder cells, differentiation inductors, or apoptosis inhibitors.

15. A method for maintaining the phenotype of a differentiated cell in a cell culture, comprising:
providing a cell culture substrate as a layer on a surface, the layer comprising a laminin, wherein the laminin is an intact protein or a protein fragment;
plating the differentiated cell directly on the cell culture substrate; and
culturing the plated differentiated cell on the layer;
whereby the phenotype of the differentiated cell is maintained in the cell culture;
wherein the differentiated cell is a cardiomyocyte; and
wherein the cell culture substrate consists of laminin-521 and/or laminin-511, or wherein the cell culture substrate consists of laminin-521 and/or laminin-511 and a cadherin, wherein each laminin is an intact protein or a protein fragment.

16. The method according to claim 15, wherein the laminin is an intact protein.

17. The method according to claim 15, wherein the cardiomyocyte is a primary cardiomyocyte.

18. The method according to claim 15, wherein the laminin is laminin-521.

19. The method according to claim 15, wherein the laminin is laminin-511.

20. The method according to claim 15, wherein the laminin is an effective recombinant laminin.

21. The method according to claim 15, further including applying a cell culture medium to the differentiated cell.

22. The method according to claim 21, wherein the cell culture medium has an albumin concentration of at least 0.3 mM.

23. The method according to claim 15, wherein the phenotype is maintained for at least 3 weeks in culture.

24. The method according to claim 15, wherein the cell culture medium does not contain any differentiation inhibitors, feeder cells, differentiation inductors, or apoptosis inhibitors.

25. The method according to claim 15, wherein the culturing is in a xeno-free and chemically defined cell culture medium.

* * * * *